(12) United States Patent
Mirzadeh et al.

(10) Patent No.: US 12,152,047 B2
(45) Date of Patent: Nov. 26, 2024

(54) ANTI-CANCER GOLD COMPOUNDS

(71) Applicant: Royal Melbourne Institute of Technology, Melbourne (AU)

(72) Inventors: Nedaossadat Mirzadeh, Melbourne (AU); Suresh Bhargava, Melbourne (AU); Steven Priver, Melbourne (AU); Srinivasa Reddy Telukutla, Melbourne (AU)

(73) Assignee: Royal Melbourne Institute of Technology, Melbourne (AU)

( * ) Notice: Subject to any disclaimer, the term of this patent is extended or adjusted under 35 U.S.C. 154(b) by 518 days.

(21) Appl. No.: 17/595,019

(22) PCT Filed: May 7, 2020

(86) PCT No.: PCT/AU2020/050451
§ 371 (c)(1),
(2) Date: Nov. 5, 2021

(87) PCT Pub. No.: WO2020/223765
PCT Pub. Date: Nov. 12, 2020

(65) Prior Publication Data
US 2022/0204538 A1 Jun. 30, 2022

(30) Foreign Application Priority Data
May 7, 2019 (AU) .................. 2019901547

(51) Int. Cl.
*C07F 9/53* (2006.01)
*A61P 35/00* (2006.01)
*C07F 1/02* (2006.01)

(52) U.S. Cl.
CPC ............ *C07F 9/5345* (2013.01); *A61P 35/00* (2018.01); *C07F 1/02* (2013.01)

(58) Field of Classification Search
CPC .. C07F 9/5345; C07F 1/02; C07F 9/58; C07F 9/6584; C07F 17/02; C07F 1/00; A61P 35/00; A61K 33/242
See application file for complete search history.

(56) References Cited

PUBLICATIONS https://dictionary.cambridge.org/us/dictionary/english/inhibit cited on May 30, 2024.*
International Search Report in PCT/AU2020/050451 issued May 26, 2020.
Gabbiani, C., et al., "Gold(III) Compounds as Anticancer Drugs." Gold Bulletin, 2007, 40(1), 73-81.
Lima, J.C., et al., "Phosphine-Gold(I) Compounds as Anticancer agents: General Description and Mechanisms of Action." Anti-Cancer Agents in Medicinal Chemistry, 2011, 11, 921-928.
Byabartta, P., "Organometallic gold(I)-pentafluorophenyl-P, O, As, S, TPA, dppm, dppe, dppa-coordinating-phosphines: synthesis and detailed spectroscopic characterization." Transition Metal Chemistry, 2007, 32, 716-726.
Taouss, C et al., "Phosphane Chalcogenides and their Metal Complexes. II. Gold(I) Halide Complexes of some Diphosphane Monochalcogenides." Z. Naturforsch. 2014, 69b, 25-48.
Breshears, A., et al., "Synthesis, spectroscopy, electrochemistry, and coordination chemistry of substituted phosphine sulfides and selenides." Polyhedron, 2015, 100, 333-343.

\* cited by examiner

*Primary Examiner* — Jessica Worsham
(74) *Attorney, Agent, or Firm* — Knobbe, Martens, Olson & Bear, LLP

(57) ABSTRACT

A compound according to Formula (I), or a pharmaceutically acceptable salt thereof:

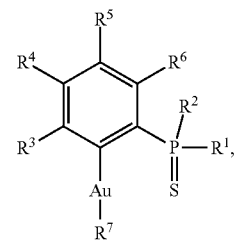

wherein $R^1$ and $R^2$ are each independently selected from optionally substituted $C_{1-6}$-alkyl and optionally substituted aryl; $R^3$, $R^4$, $R^5$, and $R^6$ are each independently selected from the group consisting of H, halo, optionally substituted $C_{1-6}$-alkyl, and optionally substituted $C_{1-6}$ alkoxy; and $R^7$ is a phosphorus containing moiety, wherein a phosphorus atom is bonded to Au.

13 Claims, 8 Drawing Sheets

ANTI-CANCER GOLD COMPOUNDS

TECHNICAL FIELD

The present invention relates to compounds comprising a gold(I) ion which are useful in the treatment of cancer.

BACKGROUND OF INVENTION

Cancer is the largest contribution (16%) to the burden of disease in Australia and is the second-leading cause of death world-wide, with an estimated 9.6 million people dying from cancer in 2018, according to the World Health Organization. The economic impact of cancer is significant and is increasing. The global annual economic cost associated with cancer is estimated to be in excess of $US 1.2 trillion although the exact cost is hard to quantify. This figure is expected to rise as life expectancy increases and as lifestyle, diet and/or environmental factors change over time.

Cancer can be described as an uncontrolled proliferation of cells, which can invade and spread to other sites of the body. The causes of cancer are generally attributed to environmental or genetic factors. More than 100 different types of cancer are known, with more new types characterised each year.

Cancer cells can exist in a number of different forms. For example, they may exist as a solid tumour, in which the cancer cells are massed together, or dispersed, as in leukemia. Cancer cells are often referred to as "malignant", because they divide endlessly, eventually crowding out nearby cells and spreading to other parts of the body. The tendency of cancer cells to spread from one organ to another or from one part of the body to another distinguishes them from benign tumour cells, which overgrow but do not spread to other organs or parts of the body. Malignant cancer cells eventually metastasize and spread to other parts of the body via the bloodstream or lymphatic system, where they can multiply and form new tumours. This sort of tumour progression makes cancer a deadly disease.

Although there have been great improvements in the diagnosis and treatment of cancer, many people still die from cancer each year. Death typically results from metastases and cancers that are resistant to conventional therapies. Current methods for the treatment of advanced and/or metastatic malignancies previously treated with chemotherapy (i.e. chemotherapy-refractory cancers) are inadequate.

Recently, there has been a growing interest in the development of metal-based compounds for the treatment of cancer, mainly because metals exhibit unique characteristics, such as redox activity, variable coordination modes and reactivity toward organic substrates, and have shown promising in vitro cytotoxic effects towards various cancer types.

Cisplatin is one of the most widely used metal-based complexes in the treatment of a variety of tumours, including cervical, ovarian, non-small cell lung carcinoma and testicular cancers. However, the clinical use of cisplatin is hampered by its toxic side-effects, drug resistance and poor solubility. These side-effects are exacerbated during the treatment of cancers which are resistant to cisplatin, since high dosages are required for efficient treatment. An example is prostate cancer, the most diagnosed cancer in Australia, the treatment of which suffers from intensified adverse side-effects due to the high dosage of cisplatin required.

New drugs are desperately needed for the treatment of cancer, as almost all drugs used today suffer from drug resistance issues and severe side effects due to a lack of selectivity towards tumours. These and other limitations have led to an intense search for new metal-based agents that show greater selectivity, lower toxicity and improved anti-cancer activity.

Therefore, two aspects in the development of new anti-cancer drugs are to maximise efficiency and to improve selectivity.

The anti-cancer properties of gold compounds, including gold(I) compounds, have gained increased attention recently as reviewed by Nardon et al., *Anticancer Res.* 2014, 34, 487; and Zou et al., *Chem. Soc. Rev.* 2015, 44, 8786.

Gold compounds offer unique opportunities to modify the properties of anti-cancer agents and to achieve selective activation in a tumour environment.

It would therefore be desirable to provide a gold-containing compound that can address or ameliorate some of the above issues or at least provide an alternative treatment option.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

SUMMARY OF THE INVENTION

Enabled herein are gold-containing compounds having anti-cancer properties, which may exhibit activity rivalling or exceeding cisplatin.

Thus, in one aspect, the present invention provides a compound according to Formula (I), or a pharmaceutically acceptable salt thereof:

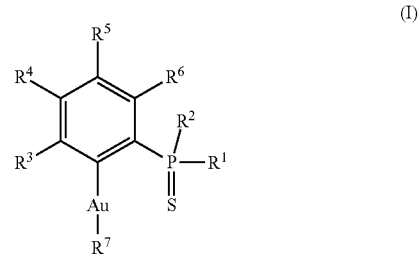

wherein: $R^1$ and $R^2$ are each independently selected from optionally substituted $C_{1-6}$-alkyl and optionally substituted aryl;

$R^3$, $R^4$, $R^5$, and $R^6$ are each independently selected from the group consisting of H, halo, optionally substituted $C_{1-6}$-alkyl, and optionally substituted $C_{1-6}$ alkoxy;

and $R^7$ is a phosphorus containing moiety, wherein a phosphorus atom is bonded to Au.

The compounds taught herein are typically stable under physiological conditions and at normal ambient temperatures, and do not require special handling in terms of storage under inert atmospheres. These compounds also display potent anti-cancer properties against a range of different cancers. In one or more embodiments, the compounds exhibit activity against cervical cancer, lung cancer, prostate cancer, and/or bone cancer.

In another aspect, the present invention provides a method of treating cancer, comprising administering to a subject in need thereof a therapeutically effective amount of a compound of Formula (I) or a pharmaceutically acceptable salt thereof.

In another aspect, the present invention provides use of a compound of Formula (I) or a pharmaceutically acceptable salt thereof, in the preparation of a medicament for the treatment of cancer.

In another aspect, the present invention provides use of a compound of Formula (I) or a pharmaceutically acceptable salt thereof for the treatment of cancer.

In another aspect, the present invention provides a compound of Formula (I) or a pharmaceutically acceptable salt thereof for use in the treatment of cancer in a subject in need thereof.

In another aspect, the present invention provides a pharmaceutical composition comprising a compound of Formula (I) or a pharmaceutically acceptable salt thereof and a pharmaceutically acceptable diluent, adjuvant excipient, or carrier.

These and other aspects of the invention and features of embodiments of the invention are illustrated in greater detail in the following description.

BRIEF DESCRIPTION OF DRAWINGS

For a further understanding of the aspects and advantages of the present invention, reference should be made to the following detailed description, taken in conjunction with the accompanying drawings.

DETAILED DESCRIPTION

Definitions

Figure 1:
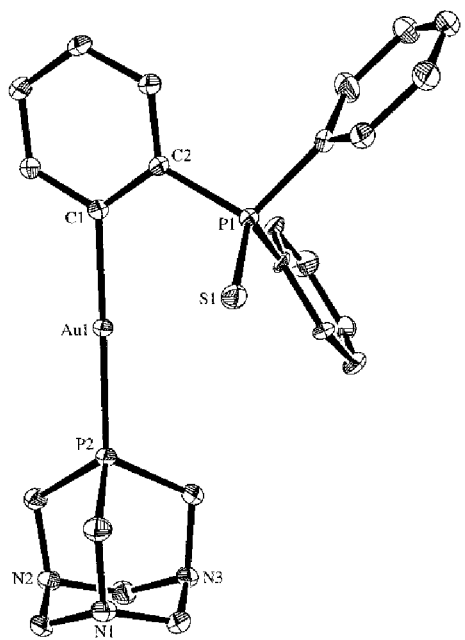
FIG. 1. Molecular structure of [Au(PTA){κC-2-$C_6H_4$P(S)$Ph_2$}] (Example 1). Ellipsoids show 50% probability levels. Hydrogen atoms and solvent of crystallisation have been omitted for clarity.
Figure 2:
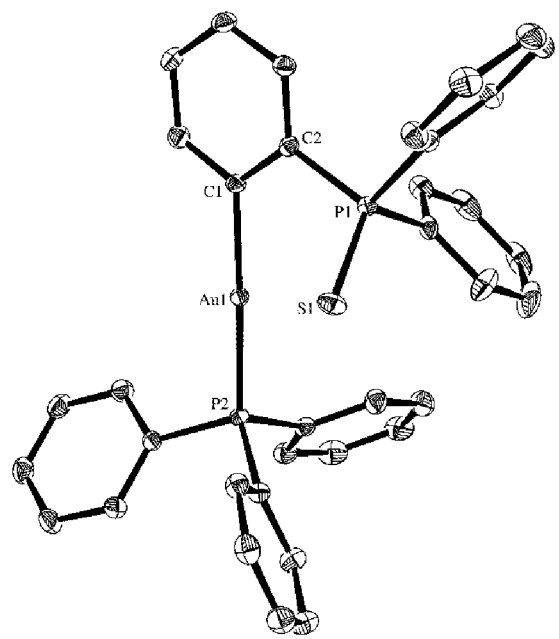
FIG. 2. Molecular structure of [Au(PPh$_3$){κC-2-$C_6H_4$P(S)$Ph_2$}] (Example 2). Ellipsoids show 50% probability levels. Hydrogen atoms and solvent of crystallisation have been omitted for clarity.
Figure 3:
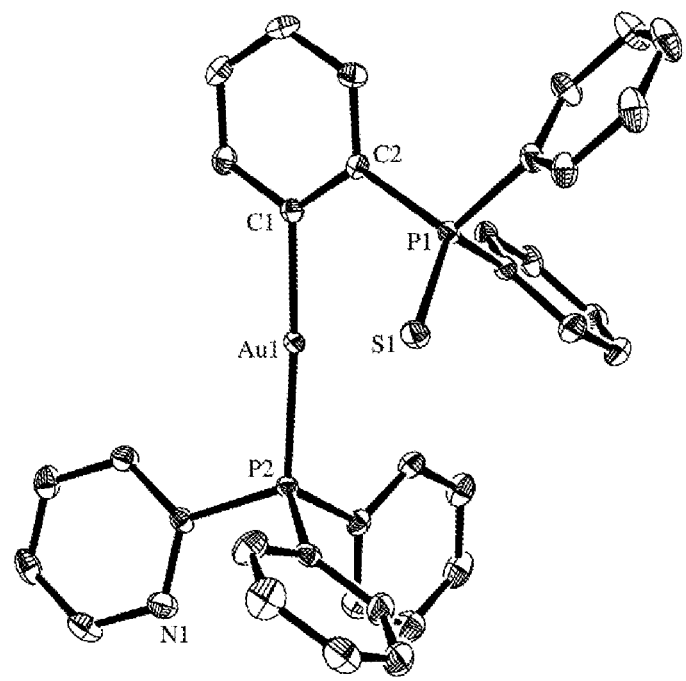
FIG. 3. Molecular structure of [Au(2-pyPPh$_2$){κC-2-$C_6H_4$P(S)$Ph_2$}]·$CH_2Cl_2$ (Example 4). Ellipsoids show 50% probability levels. Hydrogen atoms and solvent of crystallisation have been omitted for clarity. The $CH_2Cl_2$ molecule was disordered over two positions (0.6789:0.3211) and restraints were applied to the C—Cl bond lengths. The nitrogen atom in the pyPPh$_2$ ligand was also disordered over the three aromatic rings at the C26 and C32 positions (0.4435:0.1884:0.3681).
Figure 4:
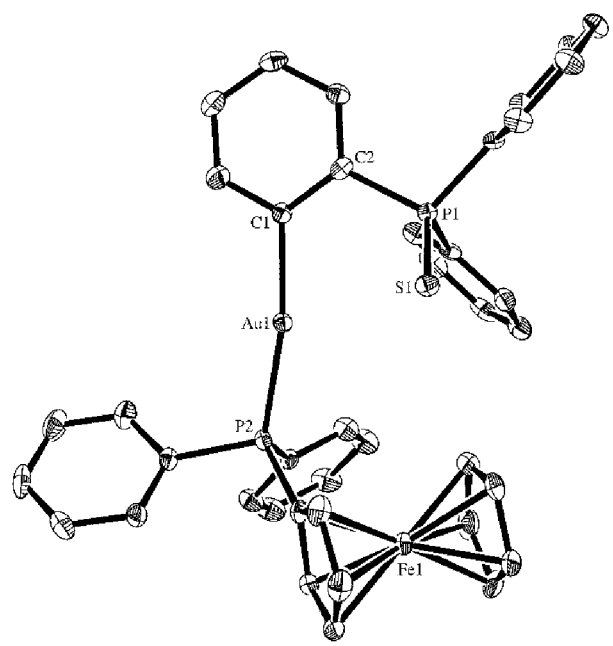
FIG. 4. Molecular structure of [Au(PPh$_2$Fc){κC-2-$C_6H_4$P(S)$Ph_2$}] (Fc=ferrocenyl) (Example 5). Ellipsoids show 50% probability levels. Hydrogen atoms and solvent of crystallisation have been omitted for clarity. The crystal is twinned and only one molecule in the asymmetric unit is shown.
Figure 5:
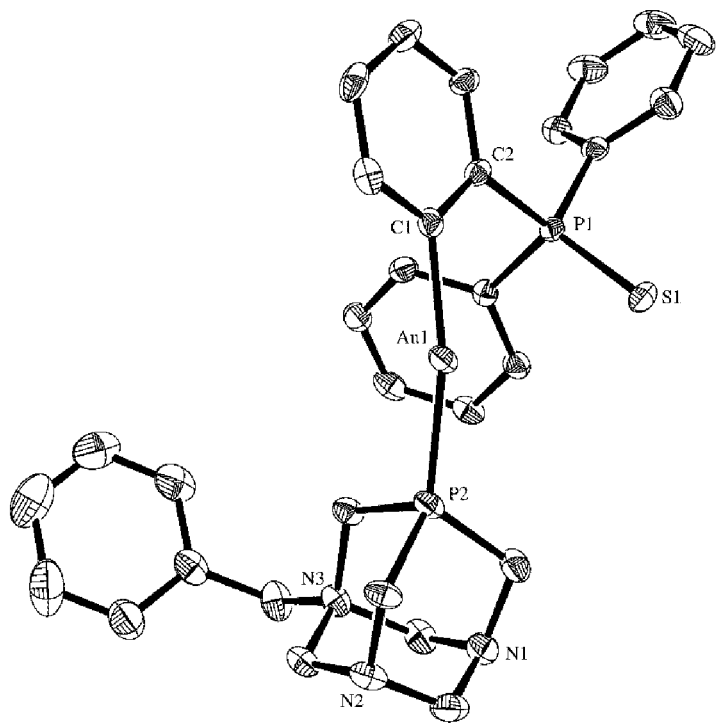
FIG. 5. Molecular structure of [Au(PTA-$CH_2$Ph){κC-2-$C_6H_4$P(S)$Ph_2$}]Br (Example 7). Ellipsoids show 50% probability levels. Hydrogen atoms, bromide counter ion and solvent of crystallisation have been omitted for clarity.
Figure 6:
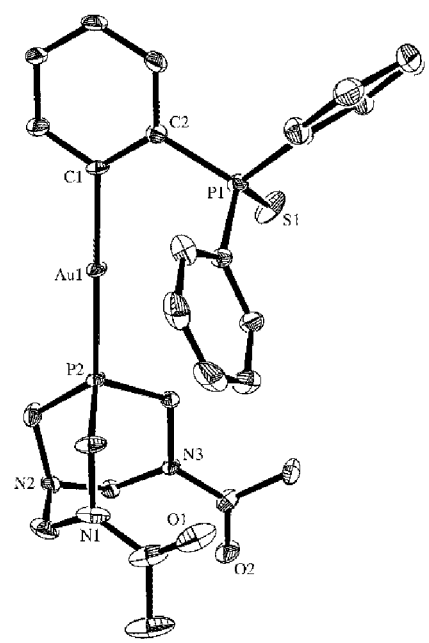
FIG. 6. Molecular structure of [Au(DAPTA){κC-2-$C_6H_4$P(S)$Ph_2$}] (Example 8). Ellipsoids show 50% probability levels. Hydrogen atoms have been omitted for clarity.
Figure 7:
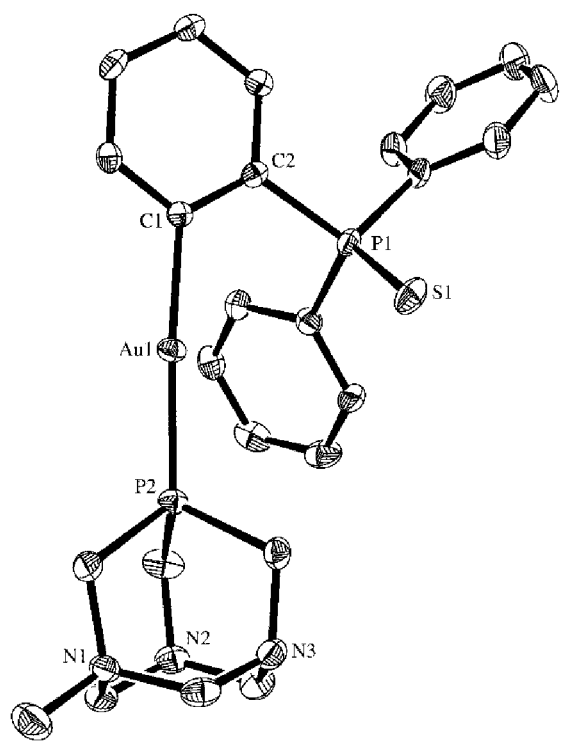
FIG. 7. Molecular structure of [Au(PTA-$CH_3$){κC-2-$C_6H_4$P(S)$Ph_2$}]PF$_6$ (Example 9). Ellipsoids show 50% probability levels. Hydrogen atoms, PF$_6$ counter ion and solvent of crystallisation have been omitted for clarity. Only one molecule in the asymmetric unit is shown.

In this specification a number of terms are used which are known to a skilled addressee. Nevertheless, for the purposes of clarity a number of terms will be defined.

As used herein, the term "optionally substituted" denotes that the group may or may not be further substituted or fused (so as to form a condensed polycyclic system), with one or more non-hydrogen substituent groups. For example, the substituent group could be one or more groups independently selected from the group consisting of halo, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, alkylalkenyl, alkylalkynyl, alkylaryl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonic acid, sulfonate, sulfonylamino, sulfinylamino, sulfonyl, alkylsulfonyl, arylsulfonyl, am inosulfonyl, sulfinyl, alkylsulfinyl, arylsulfinyl, aminosulfinylaminoalkyl, C(=O)OH, —C(=O)R$^a$, C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, $C_{1-12}$alkyl, $C_{1-12}$haloalkyl, $C_{2-12}$alkenyl, $C_{2-12}$alkynyl, $C_{1-10}$heteroalkyl, $C_{3-12}$cycloalkyl, $C_{3-12}$cycloalkenyl, $C_{1-12}$heterocycloalkyl, $C_{1-12}$heterocycloalkenyl, $C_{6-18}$aryl, $C_{1-18}$heteroaryl, and acyl, or any two or more of R$^a$, R$^b$, R$^c$ and R$^d$, when taken together with the atoms to which they are attached, form a heterocyclic ring system with 3 to 12 ring atoms.

It should be appreciated that if the optional substituent is added to a heteroatom such as a nitrogen atom (to form, for example, a quaternary nitrogen), the resulting heteroatom will be positively charged and a negatively charged counter ion will be present. It is not intended for there to be any limitation on the counter ion, insofar as the counter-ion should be pharmaceutically acceptable. Examples of counter ions include but are not limited to halide, alkoxide, mesylate, tosylate, triflate, $BF_4$, and $PF_6$.

The term "$C_{1-6}$-alkoxy" refers to a $C_{1-6}$-alkyl-O— group in which alkyl is as defined herein. Examples include, but are not limited to, methoxy, ethoxy, and propoxy.

The term "$C_{1-6}$-alkyl" refers to a straight or branched aliphatic hydrocarbon group containing from 1 to 6 carbon atoms. Examples of suitable straight and branched $C_{1-6}$-alkyl substituents include methyl, ethyl, n-propyl, 2-propyl, n-butyl, sec-butyl, t-butyl, hexyl, and the like.

The term "aryl" refers to a group or part of a group with (i) an optionally substituted monocyclic, or fused polycyclic, aromatic carbocycle (ring structure having ring atoms that are all carbon) preferably having from 5 to 12 atoms per ring; (ii) an optionally substituted partially saturated bicyclic aromatic carbocyclic moiety in which an aryl (e.g. phenyl) and a $C_{5-7}$cycloalkyl or $C_{5-7}$cycloalkenyl group are fused together to form a cyclic structure, such as tetrahydronaphthyl, indenyl or indanyl; or (iii) an optionally substituted metallocene, such as optionally substituted ferrocene. Typically an aryl group is a $C_{6-18}$ aryl group. Examples of aryl include phenyl, naphthyl, dihydroindene, indene, anthracene, and phenalene. In one embodiment, the optionally substituted aryl group is an optionally substituted phenyl group.

The term "halo", "halide" or "halogen" means fluoro, chloro, bromo or iodo.

The term "heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include but are not limited to nitrogen, oxygen and sulfur. Examples of heteroaryl include but are not limited to thiophenyl, benzothiophenyl, benzofuranyl, benzimidazolyl, benzoxazolyl, benzothiazolyl, benzisothiazolyl, naphtho[2,3-b]thiophenyl, furanyl, isoindolizinyl, xantholenyl, phenoxatinyl, pyrrolyl, imidazolyl, pyrazolyl, pyridinyl, pyrazinyl, pyrimidinyl, pyridazinyl, tetrazolyl, indolyl, isoindolyl, 1H-indazolyl, purinyl, quinolinyl, isoquinolinyl, phthalazinyl, naphthyridinyl, quinoxalinyl, cinnolinyl, carbazolyl, phenanthridinyl, acridinyl, phenazinyl, thiazolyl, isothiazolyl, phenothiazinyl, oxazolyl, isooxazolyl, furazanyl, phenoxazinyl, 2-, 3- or 4-pyridyl, 2-, 3-, 4-, 5-, or 8-quinolyl, 1-, 3-, 4-, or 5-isoquinolinyl, 1-, 2-, or 3-indolyl, and 2- or 3-thienyl. A heteroaryl group is typically a $C_1$-$C_{18}$ heteroaryl group.

The term "heterocyclic" refers to a saturated or partially unsaturated monocyclic, bicyclic or polycyclic ring system containing at least one heteroatom, such as nitrogen, sulfur, oxygen, or phosphorus as a ring atom. Each ring is preferably from 3 to 10 membered, more preferably 4 to 7 membered. Examples of suitable heterocyclic moieties include but are not limited to optionally substituted aziridinyl, azetidinyl, pyrrolidyl, piperidinyl, azepanyl, azocanyl, piperazinyl, decahydroisoquinolinyl, decahydroquinolinyl, quinuclidinyl, 1-azaadamantanyl, 2-azaadamantanyl, 1,3,5-triaza-7-phosphaadamantanyl (PTA), 3,7-diacetyl-1,3,7-triaza-5-phosphabicyclo[3.3.1]nonane (DAPTA), tetrahydrofuryl, tetrahydrothiofuranyl, tetrahydropyranyl, morphilinyl, 1,3-diazepanyl, 1,4-diazepanyl, 1,4-oxazepanyl, and 1,4-oxathiapanyl. A heterocyclic group typically is a $C_3$-$C_{12}$heterocycloalkyl group.

The term "treating" means to inhibit, reduce, diminish, arrest, or stabilize a tumour or other feature associated with cancer, or one or more symptoms thereof. Thus "treating" could result in regression or eradication of the tumour or other feature associated with cancer; or it could result in maintenance of the size of the tumour so that it does not increase, or that it increases by a lesser amount compared with a comparison therapy.

The term "cancer" refers to the uncontrolled growth of abnormal cells anywhere in a body. These abnormal cells are typically termed cancer cells, malignant cells, or tumour cells. These cells can infiltrate normal body tissues. Cancer is not confined to humans; animals and other living organisms can get cancer.

The term "administering" means to provide or apply an anti-cancer agent of the present invention to a subject in need thereof by any possible route.

The term "subject in need thereof" means a human or an animal that has or is diagnosed with cancer, or is predisposed or susceptible to cancer, or is at risk of developing cancer.

The term "therapeutically effective amount" or "effective amount" means an amount sufficient to effect beneficial or desired clinical results, such as to palliate, ameliorate, stabilize, reverse, slow or delay the progression of the cancer. An effective amount can be administered in one or more administrations.

"Pharmaceutically acceptable" means approved or approvable by a regulatory agency of the Federal or a state government or the corresponding agency in countries other than the United States, or that is listed in the U.S. Pharmacopoeia or other generally recognised pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-en-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, i.e. an alkali metal ion, an alkaline earth ion, or an aluminium ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

It is noted that the stereochemistry of the compound depicted in Formula (I) is not defined. The compounds described herein may therefore exist as single stereoisomers, racemates, and/or mixtures of enantiomers and/or diastereomers. All such single stereoisomers, racemates and mixtures thereof are intended to be within the scope of the subject matter described and claimed.

Furthermore, depending on the substitution pattern the compounds of the present invention may be capable of undergoing tautomerism. Accordingly, all such tautomers of a compound of the present invention are intended to be within the scope of the subject matter described and claimed.

Existing reports on anti-cancer gold compounds disclose compounds in which the gold atom possesses an oxidation state of I or III. One issue with gold(I) compounds is their stability under physiological conditions.

The present invention relates to a compound comprising gold(I).

Accordingly, in a first aspect of the present invention there is provided a compound according to Formula (I), or a pharmaceutically acceptable salt thereof:

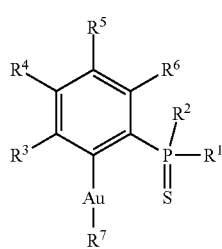

(I)

wherein $R^1$ and $R^2$ are each independently selected from optionally substituted $C_{1-6}$-alkyl and optionally substituted aryl; $R^3$, $R^4$, $R^5$, and $R^6$ are each independently selected from the group consisting of H, halo, optionally substituted $C_{1-6}$-alkyl, and optionally substituted $C_{1-6}$ alkoxy; and $R^7$ is a phosphorus containing moiety, wherein a phosphorus atom is bonded to Au.

As stated above, $R^1$ and $R^2$ may each be independently selected from optionally substituted $C_{1-6}$-alkyl. For example, $R^1$ and $R^2$ may be, independently of each other, methyl, ethyl, propyl, isopropyl, butyl, isobutyl, tert-butyl, pentyl, isopentyl, hexyl, or isohexyl. Each of $R^1$ and/or $R^2$ may also be substituted with a group as defined herein. In one embodiment, $R^1$ and $R^2$ are both ethyl.

Alternatively, $R^1$ and $R^2$ may each be independently selected from optionally substituted aryl. For example, $R^1$ and $R^2$ may be, independently of each other, phenyl or naphthyl. Each of $R^1$ and/or $R^2$ may also be substituted with a group as defined herein. In one embodiment, $R^1$ and $R^2$ are both phenyl. If $R^1$ and $R^2$ are both phenyl, there is provided a compound of Formula (II):

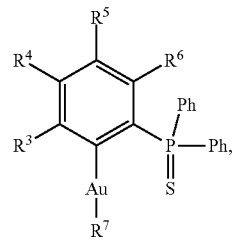

(II)

wherein $R^3$, $R^4$, $R^5$, $R^6$, and $R^7$ are as defined herein.

Alternatively, $R^1$ may be an optionally substituted $C_{1-6}$-alkyl and $R^2$ may be an optionally substituted aryl, or vice versa. For example, $R^1$ may be methyl, ethyl, propyl, isopropyl, butyl, isobutyl, tert-butyl, pentyl, isopentyl, hexyl, or isohexyl, and $R^2$ may be phenyl or naphthyl; or $R^1$ may be phenyl or naphthyl, and $R^2$ may be methyl, ethyl, propyl, isopropyl, butyl, isobutyl, tert-butyl, pentyl, isopentyl, hexyl, or isohexyl. Each of $R^1$ and/or $R^2$ may also be substituted with a group as defined herein. In one embodiment, $R^1$ is ethyl and $R^2$ is phenyl.

As stated above, $R^3$, $R^4$, $R^5$, and $R^6$ are each independently selected from the group consisting of H, halo, optionally substituted $C_{1-6}$-alkyl, and optionally substituted $C_{1-6}$ alkoxy.

In one embodiment $R^3$ is selected from the group consisting of H, Br, Cl, F, methyl, ethyl, propyl and butyl. In one embodiment $R^3$ is H. In one embodiment $R^3$ is Br. In one embodiment $R^3$ is Cl. In one embodiment $R^3$ is F. In one embodiment $R^3$ is methyl. In one embodiment $R^3$ is ethyl. In one embodiment $R^3$ is propyl. In one embodiment $R^3$ is butyl.

In one embodiment $R^4$ is selected from the group consisting of H, Br, Cl, F, methyl, ethyl, propyl and butyl. In one embodiment $R^4$ is H. In one embodiment $R^4$ is Br. In one embodiment $R^4$ is Cl. In one embodiment $R^4$ is F. In one embodiment $R^4$ is methyl. In one embodiment $R^4$ is ethyl. In one embodiment $R^4$ is propyl. In one embodiment $R^4$ is butyl.

In one embodiment $R^5$ is selected from the group consisting of H, Br, Cl, F, methyl, ethyl, propyl and butyl. In one embodiment $R^5$ is H. In one embodiment $R^5$ is Br. In one embodiment $R^5$ is Cl. In one embodiment $R^5$ is F. In one embodiment $R^5$ is methyl. In one embodiment $R^5$ is ethyl. In one embodiment $R^5$ is propyl. In one embodiment $R^5$ is butyl.

In one embodiment $R^6$ is selected from the group consisting of H, Br, Cl, F, methyl, ethyl, propyl and butyl. In one embodiment $R^6$ is H. In one embodiment $R^6$ is Br. In one embodiment $R^6$ is Cl. In one embodiment $R^6$ is F. In one embodiment $R^6$ is methyl. In one embodiment $R^6$ is ethyl. In one embodiment $R^6$ is propyl. In one embodiment $R^6$ is butyl.

In one embodiment, $R^3$, $R^4$, $R^5$, and $R^6$ are H, and $R^1$ and $R^2$ are phenyl, providing a compound of Formula (III):

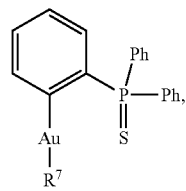

(III)

wherein $R^7$ is as defined herein.

Alternatively, $R^3$, $R^4$, $R^5$, and $R^6$ may each be halo. Examples of halo are fluoro, chloro, bromo, and iodo. In one embodiment, each of $R^3$, $R^4$, $R^5$, and $R^6$ are fluoro. In another embodiment, each of $R^3$, $R^4$, $R^5$, and $R^6$ are chloro. In another embodiment, each of $R^3$, $R^4$, $R^5$, and $R^6$ are bromo. In another embodiment, each of $R^3$, $R^4$, $R^5$, and $R^6$ are iodo. In some embodiments, one of $R^3$, $R^4$, $R^5$, or $R^6$ may be one halo while the rest are a different halo. For example, $R^3$ is fluoro and $R^4$, $R^5$, and $R^6$ are chloro; or $R^4$ is fluoro and $R^3$, $R^5$, and $R^6$ are chloro; or $R^5$ is fluoro and $R^3$, $R^4$, and $R^6$ are chloro; or $R^6$ is fluoro and $R^3$, $R^4$, and $R^5$ are chloro; or $R^3$ is bromo and $R^4$, $R^5$, and $R^6$ are chloro; or $R^4$ is bromo and $R^3$, $R^5$, and $R^6$ are chloro; or $R^5$ is bromo and $R^3$, $R^4$, and $R^6$ are chloro; or $R^6$ is bromo and $R^3$, $R^4$, and $R^5$ are chloro; or $R^3$ is iodo and $R^4$, $R^5$, and $R^6$ are chloro; or $R^4$ is iodo and $R^3$, $R^5$, and $R^6$ are chloro; or $R^5$ is iodo and $R^3$, $R^4$, and $R^6$ are chloro; or $R^6$ is iodo and $R^3$, $R^4$, and $R^5$ are chloro. Alternatively, two of $R^3$, $R^4$, $R^5$, or $R^6$ may be one halo while the other two are a different halo. For example, $R^3$ and $R^4$ are fluoro and $R^5$ and $R^6$ are chloro; or $R^3$ and $R^5$ are fluoro and $R^4$ and $R^6$ are chloro; or $R^3$ and $R^6$ are fluoro and $R^4$ and $R^5$ are chloro; or $R^3$ and $R^4$ are chloro and $R^5$ and $R^6$ are fluoro; or $R^3$ and $R^4$ are chloro and $R^5$ and $R^6$ are fluoro; or $R^3$ and $R^5$ are chloro and $R^4$ and $R^6$ are fluoro; or $R^3$ and $R^6$ are chloro and $R^4$ and $R^5$ are fluoro; or $R^3$ and $R^4$ are chloro and $R^5$ and $R^6$ are fluoro. Alternatively, $R^3$, $R^4$, $R^5$, or $R^6$ may be comprised of three or four different halogens. For example, $R^1$ is fluoro, $R^2$ chloro, $R^3$ is bromo, and $R^4$ is iodo; or $R^1$ is chloro, $R^2$ bromo, $R^3$ is iodo, and $R^4$ is fluoro; or $R^1$ is bromo, $R^2$ iodo, $R^3$ is fluoro, and $R^4$ is chloro; or $R^1$ is iodo, $R^2$ fluoro, $R^3$ is chloro, and $R^4$ is bromo.

Alternatively, $R^3$, $R^4$, $R^5$, and $R^6$ may each be optionally substituted $C_{1-6}$-alkyl. For example, each $R^3$, $R^4$, $R^5$, and $R^6$ is methyl; or each $R^3$, $R^4$, $R^5$, and $R^6$ is ethyl; or each $R^3$, $R^4$, $R^5$, and $R^6$ is propyl; or each $R^3$, $R^4$, $R^5$, and $R^6$ is butyl; or each $R^3$, $R^4$, $R^5$, and $R^6$ is pentyl; or each $R^3$, $R^4$, $R^5$, and $R^6$ is hexyl. In some embodiments, one of $R^3$, $R^4$, $R^5$, or $R^6$ may be one optionally substituted $C_{1-6}$-alkyl while the rest are a different optionally substituted $C_{1-6}$-alkyl. For example, $R^3$ is methyl and $R^4$, $R^5$, and $R^6$ are ethyl; or $R^4$ is methyl and $R^3$, $R^5$, and $R^6$ are ethyl; or $R^5$ is methyl and $R^3$, $R^4$, and $R^6$ are ethyl; or $R^6$ is methyl and $R^3$, $R^4$, and $R^5$ are ethyl; or $R^3$ is ethyl and $R^4$, $R^5$, and $R^6$ are methyl; or $R^4$ is ethyl and $R^3$, $R^5$, and $R^6$ are methyl; or $R^5$ is ethyl and $R^3$, $R^4$, and $R^6$ are methyl; or $R^6$ is ethyl and $R^3$, $R^4$, and $R^5$ are methyl. Alternatively, two of $R^3$, $R^4$, $R^5$, or $R^6$ may be one optionally substituted $C_{1-6}$-alkyl while the other two are a different optionally substituted $C_{1-6}$-alkyl. For example, $R^3$ and $R^4$ are methyl and $R^5$ and $R^6$ are ethyl; or $R^3$ and $R^5$ are methyl and $R^4$ and $R^6$ are ethyl; or $R^3$ and $R^6$ are methyl and $R^4$ and $R^5$ are ethyl; or $R^3$ and $R^4$ are methyl and $R^5$ and $R^6$ are methyl. Alternatively, $R^3$, $R^4$, $R^5$, or $R^6$ may be comprised of three or four different optionally substituted $C_{1-6}$-alkyl. For example, $R^1$ is methyl, $R^2$ ethyl, $R^3$ is propyl, and $R^4$ is butyl; or $R^1$ is ethyl, $R^2$ propyl, $R^3$ is butyl, and $R^4$ is methyl; or $R^1$ is propyl, $R^2$ butyl, $R^3$ is methyl, and $R^4$ is ethyl; or $R^1$ is butyl, $R^2$ methyl, $R^3$ is ethyl, and $R^4$ is propyl.

Alternatively, $R^3$, $R^4$, $R^5$, and $R^6$ may each be optionally substituted $C_{1-6}$-alkoxy. For example, each $R^3$, $R^4$, $R^5$, and $R^6$ is methoxy; or each $R^3$, $R^4$, $R^5$, and $R^6$ is ethoxy; or each $R^3$, $R^4$, $R^5$, and $R^6$ is propoxy; or each $R^3$, $R^4$, $R^5$, and $R^6$ is butoxy; or each $R^3$, $R^4$, $R^5$, and $R^6$ is pentyloxy; or each $R^3$, $R^4$, $R^5$, and $R^6$ is hexyloxy. In some embodiments, one of $R^3$, $R^4$, $R^5$, or $R^6$ may be one optionally substituted $C_{1-6}$-alkoxy while the rest are a different optionally substituted $C_{1-6}$-alkoxy. For example, $R^3$ is methoxy and $R^4$, $R^5$, and $R^6$ are ethoxy; or $R^4$ is methoxy and $R^3$, $R^5$, and $R^6$ are ethoxy; or $R^5$ is methoxy and $R^3$, $R^4$, and $R^6$ are ethoxy; or $R^6$ is methoxy and $R^3$, $R^4$, and $R^5$ are ethoxy; or $R^3$ is ethoxy and $R^4$, $R^5$, and $R^6$ are methoxy; or $R^4$ is ethoxy and $R^3$, $R^5$, and $R^6$ are methoxy; or $R^5$ is ethoxy and $R^3$, $R^4$, and $R^6$ are methoxy; or $R^6$ is ethoxy and $R^3$, $R^4$, and $R^5$ are methoxy. Alternatively, two of $R^3$, $R^4$, $R^5$, or $R^6$ may be one optionally substituted $C_{1-6}$-alkoxy while the other two are a different optionally substituted $C_{1-6}$-alkoxy. For example, $R^3$ and $R^4$ are methoxy and $R^5$ and $R^6$ are ethoxy; or $R^3$ and $R^5$ are methoxy and $R^4$ and $R^6$ are ethoxy; or $R^3$ and $R^6$ are methoxy and $R^4$ and $R^5$ are ethoxy; or $R^3$ and $R^4$ are methoxy and $R^5$ and $R^6$ are methoxy. Alternatively, $R^3$, $R^4$, $R^5$, or $R^6$ may be comprised of three or four different optionally substituted $C_{1-6}$-alkoxy. For example, $R^1$ is methoxy, $R^2$ ethoxy, $R^3$ is propoxy, and $R^4$ is butoxy; or $R^1$ is ethoxy, $R^2$ propoxy, $R^3$ is butoxy, and $R^4$ is methoxy; or $R^1$ is propoxy, $R^2$ butoxy, $R^3$ is methoxy, and $R^4$ is ethoxy; or $R^1$ is butoxy, $R^2$ methoxy, $R^3$ is ethoxy, and $R^4$ is propoxy.

Alternatively, $R^3$, $R^4$, $R^5$, and $R^6$ may represent different moieties selected from the group consisting of H, halo, optionally substituted $C_{1-6}$-alkyl, and optionally substituted $C_{1-6}$ alkoxy in any combination. For example, $R^3$, $R^4$, $R^5$, and $R^6$ may be comprised of H and halogen, such as when $R^3$, $R^4$, and $R^5$ are H and $R^6$ is fluoro; or $R^3$, $R^4$, and $R^5$ are H and $R^6$ is chloro; or $R^3$, $R^4$, and $R^5$ are H and $R^6$ is bromo; or $R^3$, $R^4$, and $R^5$ are H and $R^6$ is iodo; or $R^3$, $R^4$, and $R^6$ are H and $R^5$ is fluoro; or $R^3$, $R^4$, and $R^6$ are H and $R^5$ is chloro; or $R^3$, $R^4$, and $R^6$ are H and $R^5$ is bromo; or $R^3$, $R^4$, and $R^6$ are H and $R^5$ is iodo; or $R^3$, $R^5$, and $R^6$ are H and $R^4$ is fluoro; or $R^3$, $R^5$, and $R^6$ are H and $R^4$ is chloro; or $R^3$, $R^5$, and $R^6$ are H and $R^4$ is bromo; or $R^3$, $R^5$, and $R^6$ are H and $R^4$ is iodo; or $R^4$, $R^5$, and $R^6$ are H and $R^3$ is fluoro; or $R^4$, $R^5$, and $R^6$ are H and $R^3$ is chloro; or $R^4$, $R^5$, and $R^6$ are H and $R^3$ is bromo; or $R^4$, $R^5$, and $R^6$ are H and $R^3$ is iodo; or $R^3$ and $R^4$ are H and $R^5$ and $R^6$ are fluoro; or $R^3$ and $R^5$ are H and $R^4$ and $R^6$ are fluoro; or $R^3$ and $R^6$ are H and $R^4$ and $R^5$ are fluoro; or $R^4$ and $R^5$ are H and $R^3$ and $R^6$ are fluoro; or $R^4$ and $R^6$ are H and $R^3$ and $R^5$ are fluoro; or $R^5$ and $R^6$ are H and $R^3$ and $R^4$ are fluoro; or $R^3$ and $R^4$ are H and $R^5$ and $R^6$ are chloro; or $R^3$ and $R^5$ are H and $R^4$ and $R^6$ are chloro; or $R^3$ and $R^6$ are H and $R^4$ and $R^5$ are chloro; or $R^4$ and $R^5$ are H and $R^3$ and $R^6$ are chloro; or $R^4$ and $R^6$ are H and $R^3$ and $R^5$ are chloro; or $R^5$ and $R^6$ are H and $R^3$ and $R^4$ are chloro; or $R^3$ and $R^4$ are H and $R^5$ and $R^6$ are bromo; or $R^3$ and $R^5$ are H and $R^4$ and $R^6$ are bromo; or $R^3$ and $R^6$ are H and $R^4$ and $R^5$ are bromo; or $R^4$ and $R^5$ are H and $R^3$ and $R^6$ are bromo; or $R^4$ and $R^6$ are H and $R^3$ and $R^5$ are bromo; or $R^5$ and $R^6$ are H and $R^3$ and $R^4$ are bromo; or $R^3$ and $R^4$ are H and $R^5$ and $R^6$ are iodo; or $R^3$ and $R^5$ are H and $R^4$ and $R^6$ are iodo; or $R^3$ and $R^6$ are H and $R^4$ and $R^5$ are iodo; or $R^4$ and $R^5$ are H and $R^3$ and $R^6$ are iodo; or $R^4$ and $R^6$ are H and $R^3$ and $R^5$ are iodo; or $R^5$ and $R^6$ are H and $R^3$ and $R^4$ are iodo; or $R^3$, $R^4$, and $R^5$ are fluoro and $R^6$ is H; or $R^3$, $R^4$, and $R^5$ are chloro and $R^6$ is H; or $R^3$, $R^4$, and $R^5$ are bromo and $R^6$ is H; or $R^3$, $R^4$, and $R^5$ are iodo and $R^6$ is H; or $R^3$, $R^4$, and $R^6$ are fluoro and $R^5$ is H; or $R^3$, $R^4$, and $R^6$ are chloro and $R^5$ is H; or $R^3$, $R^4$, and $R^6$ are bromo and $R^5$ is H; or $R^3$, $R^4$, and $R^6$ are iodo and $R^5$ is H; or $R^3$, $R^5$, and $R^6$ are fluoro and $R^4$ is H; or $R^3$, $R^5$, and $R^6$ are chloro and $R^4$ is H; or $R^3$, $R^5$, and $R^6$ are bromo and $R^4$ is H; or $R^3$, $R^5$, and $R^6$ are iodo and $R^4$ is H; or $R^4$, $R^5$, and $R^6$ are fluoro and $R^3$ is H; or $R^4$, $R^5$, and $R^6$ are chloro and $R^3$ is H; or $R^4$, $R^5$, and $R^6$ are bromo and $R^3$ is H; or $R^4$, $R^5$, and $R^6$ are iodo and $R^3$ is H.

Alternatively, $R^3$, $R^4$, $R^5$, and $R^6$ may be comprised of H and optionally substituted $C_{1-6}$-alkyl, such as when $R^3$, $R^4$, and $R^5$ are H and $R^6$ is methyl; or $R^3$, $R^4$, and $R^5$ are H and $R^6$ is ethyl; or $R^3$, $R^4$, and $R^5$ are H and $R^6$ is propyl; or $R^3$, $R^4$, and $R^5$ are H and $R^6$ is butyl; or $R^3$, $R^4$, and $R^6$ are H and $R^5$ is methyl; or $R^3$, $R^4$, and $R^6$ are H and $R^5$ is ethyl; or $R^3$, $R^4$, and $R^6$ are H and $R^5$ is propyl; or $R^3$, $R^4$, and $R^6$ are H and $R^5$ is butyl; or $R^3$, $R^5$, and $R^6$ are H and $R^4$ is methyl; or $R^3$, $R^5$, and $R^6$ are H and $R^4$ is ethyl; or $R^3$, $R^5$, and $R^6$ are H and $R^4$ is propyl; or $R^3$, $R^5$, and $R^6$ are H and $R^4$ is butyl; or $R^4$, $R^5$, and $R^6$ are H and $R^3$ is methyl; or $R^4$, $R^5$, and $R^6$ are H and $R^3$ is ethyl; or $R^4$, $R^5$, and $R^6$ are H and $R^3$ is propyl; or $R^4$, $R^5$, and $R^6$ are H and $R^3$ is butyl; or $R^3$ and $R^4$ are H and $R^5$ and $R^6$ are methyl; or $R^3$ and $R^5$ are H and $R^4$ and $R^6$ are methyl; or $R^3$ and $R^6$ are H and $R^4$ and $R^5$ are methyl; or $R^4$ and $R^5$ are H and $R^3$ and $R^6$ are methyl; or $R^4$ and $R^6$ are H and $R^3$ and $R^5$ are methyl; or $R^5$ and $R^6$ are H and $R^3$ and $R^4$ are methyl; or $R^3$ and $R^4$ are H and $R^5$ and $R^6$ are ethyl; or $R^3$ and $R^5$ are H and $R^4$ and $R^6$ are ethyl; or $R^3$ and $R^6$ are H and $R^4$ and $R^5$ are ethyl; or $R^4$ and $R^5$ are H and $R^3$ and $R^6$ are ethyl; or $R^4$ and $R^6$ are H and $R^3$ and $R^5$ are ethyl; or $R^5$ and $R^6$ are H and $R^3$ and $R^4$ are ethyl; or $R^3$ and $R^4$ are H and $R^5$ and $R^6$ are propyl; or $R^3$ and $R^5$ are H and $R^4$ and $R^6$ are propyl; or $R^3$ and $R^6$ are H and $R^4$ and $R^5$ are propyl; or $R^4$ and $R^5$ are H and $R^3$ and $R^6$ are propyl; or $R^4$ and $R^6$ are H and $R^3$ and $R^5$ are propyl; or $R^5$ and $R^6$ are H and $R^3$ and $R^4$ are propyl; or $R^3$ and $R^4$ are H and $R^5$ and $R^6$ are butyl; or $R^3$ and $R^5$ are H and $R^4$ and $R^6$ are butyl; or $R^3$ and $R^6$ are H and $R^4$ and $R^5$ are butyl; or $R^4$ and $R^5$ are H and $R^3$ and $R^6$ are butyl; or $R^4$ and $R^6$ are H and $R^3$ and $R^5$ are butyl; or $R^5$ and $R^6$ are H and $R^3$ and $R^4$ are butyl; or $R^3$, $R^4$, and $R^5$ are methyl and $R^6$ is H; or $R^3$, $R^4$, and $R^5$ are ethyl and $R^6$ is H; or $R^3$, $R^4$, and $R^5$ are propyl and $R^6$ is H; or $R^3$, $R^4$, and $R^5$ are butyl and $R^6$ is H; or $R^3$, $R^4$, and $R^6$ are methyl and $R^5$ is H; or $R^3$, $R^4$, and $R^6$ are ethyl and $R^5$ is H; or $R^3$, $R^4$, and $R^6$ are propyl and $R^5$ is H; or $R^3$, $R^4$, and $R^6$ are butyl and $R^5$ is H; or $R^3$, $R^5$, and $R^6$ are methyl and $R^4$ is H; or $R^3$, $R^5$, and $R^6$ are ethyl and $R^4$ is H; or $R^3$, $R^5$, and $R^6$ are propyl and $R^4$ is H; or $R^3$, $R^5$, and $R^6$ are butyl and $R^4$ is H; or $R^4$, $R^5$, and $R^6$ are methyl and $R^3$ is H; or $R^4$, $R^5$, and $R^6$ are ethyl and $R^3$ is H; or $R^4$, $R^5$, and $R^6$ are propyl and $R^3$ is H; or $R^4$, $R^5$, and $R^6$ are butyl and $R^3$ is H.

Alternatively, $R^3$, $R^4$, $R^5$, and $R^6$ may be comprised of H and optionally substituted $C_{1-6}$-alkoxy, such as when $R^3$, $R^4$, and $R^5$ are H and $R^6$ is methoxy; or $R^3$, $R^4$, and $R^5$ are H and $R^6$ is ethoxy; or $R^3$, $R^4$, and $R^5$ are H and $R^6$ is propoxy; or $R^3$, $R^4$, and $R^5$ are H and $R^6$ is butoxy; or $R^3$, $R^4$, and $R^6$ are H and $R^5$ is methoxy; or $R^3$, $R^4$, and $R^6$ are H and $R^5$ is ethoxy; or $R^3$, $R^4$, and $R^6$ are H and $R^5$ is propoxy; or $R^3$, $R^4$, and $R^6$ are H and $R^5$ is butoxy; or $R^3$, $R^5$, and $R^6$ are H and $R^4$ is methoxy; or $R^3$, $R^5$, and $R^6$ are H and $R^4$ is ethoxy; or $R^3$, $R^5$, and $R^6$ are H and $R^4$ is propoxy; or $R^3$, $R^5$, and $R^6$ are H and $R^4$ is butoxy; or $R^4$, $R^5$, and $R^6$ are H and $R^3$ is methoxy; or $R^4$, $R^5$, and $R^6$ are H and $R^3$ is ethoxy; or $R^4$, $R^5$, and $R^6$ are H and $R^3$ is propoxy; or $R^4$, $R^5$, and $R^6$ are H and $R^3$ is butoxy; or $R^3$ and $R^4$ are H and $R^5$ and $R^6$ are methoxy; or $R^3$ and $R^5$ are H and $R^4$ and $R^6$ are methoxy; or $R^3$ and $R^6$ are H and $R^4$ and $R^5$ are methoxy; or $R^4$ and $R^5$ are H and $R^3$ and $R^6$ are methoxy; or $R^4$ and $R^6$ are H and $R^3$ and $R^5$ are methoxy; or $R^5$ and $R^6$ are H and $R^3$ and $R^4$ are methoxy; or $R^3$ and $R^4$ are H and $R^5$ and $R^6$ are ethoxy; or $R^3$ and $R^5$ are H and $R^4$ and $R^6$ are ethoxy; or $R^3$ and $R^6$ are H and $R^4$ and $R^5$ are ethoxy; or $R^4$ and $R^5$ are H and $R^3$ and $R^6$ are ethoxy; or $R^4$ and $R^6$ are H and $R^3$ and $R^5$ are ethoxy; or $R^5$ and $R^6$ are H and $R^3$ and $R^4$ are ethoxy; or $R^3$ and $R^4$ are H and $R^5$ and $R^6$ are propoxy; or $R^3$ and $R^5$ are H and $R^4$ and $R^6$ are propoxy; or $R^3$ and $R^6$ are H and $R^4$ and $R^5$ are propoxy; or $R^4$ and $R^5$ are H and $R^3$ and $R^6$ are propoxy; or $R^4$ and $R^6$ are H and $R^3$ and $R^5$ are propoxy; or $R^5$ and $R^6$ are H and $R^3$ and $R^4$ are propoxy; or $R^3$ and $R^4$ are H and $R^5$ and $R^6$ are butoxy; or $R^3$ and $R^5$ are H and $R^4$ and $R^6$ are butoxy; or $R^3$ and $R^6$ are H and $R^4$ and $R^5$ are butoxy; or $R^4$ and $R^5$ are H and $R^3$ and $R^6$ are butoxy; or $R^4$ and $R^6$ are H and $R^3$ and $R^5$ are butoxy; or $R^5$ and $R^6$ are H and $R^3$ and $R^4$ are butoxy; or $R^3$, $R^4$, and $R^5$ are methoxy and $R^6$ is H; or $R^3$, $R^4$, and $R^5$ are ethoxy and $R^6$ is H; or $R^3$, $R^4$, and $R^5$ are propoxy and $R^6$ is H; or $R^3$, $R^4$, and $R^5$ are butoxy and $R^6$ is H; or $R^3$, $R^4$, and $R^6$ are methoxy and $R^5$ is H; or $R^3$, $R^4$, and $R^6$ are ethoxy and $R^5$ is H; or $R^3$, $R^4$, and $R^6$ are propoxy and $R^5$ is H; or $R^3$, $R^4$, and $R^6$ are butoxy and $R^5$ is H; or $R^3$, $R^5$, and $R^6$ are methoxy and $R^4$ is H; or $R^3$, $R^5$, and $R^6$ are ethoxy and $R^4$ is H; or $R^3$, $R^5$, and $R^6$ are propoxy and $R^4$ is H; or $R^3$, $R^5$, and $R^6$ are butoxy and $R^4$ is H; or $R^4$, $R^5$, and $R^6$ are methoxy and $R^3$ is H; or $R^4$, $R^5$, and $R^6$ are ethoxy and $R^3$ is H; or $R^4$, $R^5$, and $R^6$ are propoxy and $R^3$ is H; or $R^4$, $R^5$, and $R^6$ are butoxy and $R^3$ is H.

Alternatively, $R^3$, $R^4$, $R^5$, and $R^6$ may be comprised of halo and optionally substituted $C_{1-6}$-alkyl, such as when $R^3$, $R^4$, and $R^5$ are fluoro and $R^6$ is methyl; or $R^3$, $R^4$, and $R^5$ are fluoro and $R^6$ is ethyl; or $R^3$, $R^4$, and $R^5$ are fluoro and $R^6$ is propyl; or $R^3$, $R^4$, and $R^5$ are fluoro and $R^6$ is butyl; or $R^3$, $R^4$, and $R^6$ are fluoro and $R^5$ is methyl; or $R^3$, $R^4$, and $R^6$ are fluoro and $R^5$ is ethyl; or $R^3$, $R^4$, and $R^6$ are fluoro and $R^5$ is propyl; or $R^3$, $R^4$, and $R^6$ are fluoro and $R^5$ is butyl; or $R^3$, $R^5$, and $R^6$ are fluoro and $R^4$ is methyl; or $R^3$, $R^5$, and $R^6$ are fluoro and $R^4$ is ethyl; or $R^3$, $R^5$, and $R^6$ are fluoro and $R^4$ is propyl; or $R^3$, $R^5$, and $R^6$ are fluoro and $R^4$ is butyl; or $R^4$, $R^5$, and $R^6$ are fluoro and $R^3$ is methyl; or $R^4$, $R^5$, and $R^6$ are fluoro and $R^3$ is ethyl; or $R^4$, $R^5$, and $R^6$ are fluoro and $R^3$ is propyl; or $R^4$, $R^5$, and $R^6$ are fluoro and $R^3$ is butyl; or $R^3$ and $R^4$ are fluoro and $R^5$ and $R^6$ are methyl; or $R^3$ and $R^5$ are fluoro and $R^4$ and $R^6$ are methyl; or $R^3$ and $R^6$ are fluoro and $R^4$ and $R^5$ are methyl; or $R^4$ and $R^5$ are fluoro and $R^3$ and $R^6$ are methyl; or $R^4$ and $R^6$ are fluoro and $R^3$ and $R^5$ are methyl; or $R^5$ and $R^6$ are fluoro and $R^3$ and $R^4$ are methyl; or $R^3$ and $R^4$ are fluoro and $R^5$ and $R^6$ are ethyl; or $R^3$ and $R^5$ are fluoro and $R^4$ and $R^6$ are ethyl; or $R^3$ and $R^6$ are fluoro and $R^4$ and $R^5$ are ethyl; or $R^4$ and $R^5$ are fluoro and $R^3$ and $R^6$ are ethyl; or $R^4$ and $R^6$ are fluoro and $R^3$ and $R^5$ are ethyl; or $R^5$ and $R^6$ are fluoro and $R^3$ and $R^4$ are ethyl; or $R^3$ and $R^4$ are fluoro and $R^5$ and $R^6$ are propyl; or $R^3$ and $R^5$ are fluoro and $R^4$ and $R^6$ are propyl; or $R^3$ and $R^6$ are fluoro and $R^4$ and $R^5$ are propyl; or $R^4$ and $R^5$ are fluoro and $R^3$ and $R^6$ are propyl; or $R^4$ and $R^6$ are fluoro and $R^3$ and $R^5$ are propyl; or $R^5$ and $R^6$ are fluoro and $R^3$ and $R^4$ are propyl; or $R^3$ and $R^4$ are fluoro and $R^5$ and $R^6$ are butyl; or $R^3$ and $R^5$ are fluoro and $R^4$ and $R^6$ are butyl; or $R^3$ and $R^6$ are fluoro and $R^4$ and $R^5$ are butyl; or $R^4$ and $R^5$ are fluoro and $R^3$ and $R^6$ are butyl; or $R^4$ and $R^6$ are fluoro and $R^3$ and $R^5$ are butyl; or $R^5$ and $R^6$ are fluoro and $R^3$ and $R^4$ are butyl; or $R^3$, $R^4$, and $R^5$ are methyl and $R^6$ is fluoro; or $R^3$, $R^4$, and $R^5$ are ethyl and $R^6$ is fluoro; or $R^3$, $R^4$, and $R^5$ are propyl and $R^6$ is fluoro; or $R^3$, $R^4$, and $R^5$ are butyl and $R^6$ is fluoro; or $R^3$, $R^4$, and $R^6$ are methyl and $R^5$ is fluoro; or $R^3$, $R^4$, and $R^6$ are ethyl and $R^5$ is fluoro; or $R^3$, $R^4$, and $R^6$ are propyl and $R^5$ is fluoro; or $R^3$, $R^4$, and $R^6$ are butyl and $R^5$ is fluoro; or $R^3$, $R^5$, and $R^6$ are methyl and $R^4$ is fluoro; or $R^3$, $R^5$, and $R^6$ are ethyl and $R^4$ is fluoro; or $R^3$, $R^5$, and $R^6$ are propyl and $R^4$ is fluoro; or $R^3$, $R^5$, and $R^6$ are butyl and $R^4$ is fluoro; or $R^4$, $R^5$, and $R^6$ are methyl and $R^3$ is fluoro; or $R^4$, $R^5$, and $R^6$ are ethyl and $R^3$ is fluoro; or $R^4$, $R^5$, and $R^6$ are propyl and $R^3$ is fluoro; or $R^4$, $R^5$, and $R^6$ are butyl and $R^3$ is fluoro; or $R^3$, $R^4$, and $R^5$ are chloro and $R^6$ is methyl; or $R^3$, $R^4$, and $R^5$ are chloro and $R^6$ is ethyl; or $R^3$, $R^4$, and $R^5$ are chloro and $R^6$ is propyl; or $R^3$, $R^4$, and $R^5$ are chloro and $R^6$ is butyl; or $R^3$, $R^4$, and $R^6$ are chloro and $R^5$ is methyl; or $R^3$, $R^4$, and $R^6$ are chloro and $R^5$ is ethyl; or $R^3$, $R^4$, and $R^6$ are chloro and $R^5$ is propyl; or $R^3$, $R^4$, and $R^6$ are chloro and $R^5$ is butyl; or $R^3$, $R^5$, and $R^6$ are chloro and $R^4$ is methyl; or $R^3$, $R^5$, and $R^6$ are chloro and $R^4$ is ethyl; or $R^3$, $R^5$, and $R^6$ are chloro and $R^4$ is propyl; or $R^3$, $R^5$, and $R^6$ are chloro and $R^4$ is butyl; or $R^4$, $R^5$, and $R^6$ are chloro and $R^3$ is methyl; or $R^4$, $R^5$, and $R^6$ are chloro and $R^3$ is ethyl; or $R^4$, $R^5$, and $R^6$ are chloro and $R^3$ is propyl; or $R^4$, $R^5$, and $R^6$ are chloro and $R^3$ is butyl; or $R^3$ and $R^4$ are chloro and $R^5$ and $R^6$ are methyl; or $R^3$ and $R^5$ are chloro and $R^4$ and $R^6$ are methyl; or $R^3$ and $R^6$ are chloro and $R^4$ and $R^5$ are methyl; or $R^4$ and $R^5$ are chloro and $R^3$ and $R^6$ are methyl; or $R^4$ and $R^6$ are chloro and $R^3$ and $R^5$ are methyl; or $R^5$ and $R^6$ are chloro and $R^3$ and $R^4$ are methyl; or $R^3$ and $R^4$ are chloro and $R^5$ and $R^6$ are ethyl; or $R^3$ and $R^5$ are chloro and $R^4$ and $R^6$ are ethyl; or $R^3$ and $R^6$ are chloro and $R^4$ and $R^5$ are ethyl; or $R^4$ and $R^5$ are chloro and $R^3$ and $R^6$ are ethyl; or $R^4$ and $R^6$ are chloro and $R^3$ and $R^5$ are ethyl; or $R^5$ and $R^6$ are chloro and $R^3$ and $R^4$ are ethyl; or $R^3$ and $R^4$ are chloro and $R^5$ and $R^6$ are propyl; or $R^3$ and $R^5$ are chloro and $R^4$ and $R^6$ are propyl; or $R^3$ and $R^6$ are chloro and $R^4$ and $R^5$ are propyl; or $R^4$ and $R^5$ are chloro and $R^3$ and $R^6$ are propyl; or $R^4$ and $R^6$ are chloro and $R^3$ and $R^5$ are propyl; or $R^5$ and $R^6$ are chloro and $R^3$ and $R^4$ are propyl; or $R^3$ and $R^4$ are chloro and $R^5$ and $R^6$ are butyl; or $R^3$ and $R^5$ are chloro and $R^4$ and $R^6$ are butyl; or $R^3$ and $R^6$ are chloro and $R^4$ and $R^5$ are butyl; or $R^4$ and $R^5$ are chloro and $R^3$ and $R^6$ are butyl; or $R^4$ and $R^6$ are chloro and $R^3$ and $R^5$ are butyl; or $R^5$ and $R^6$ are chloro and $R^3$ and $R^4$ are butyl; or $R^3$, $R^4$, and $R^5$ are methyl and $R^6$ is chloro; or $R^3$, $R^4$, and $R^5$ are ethyl and $R^6$ is chloro; or $R^3$, $R^4$, and $R^5$ are propyl and $R^6$ is chloro; or $R^3$, $R^4$, and $R^5$ are butyl and $R^6$ is chloro; or $R^3$, $R^4$, and $R^6$ are methyl and $R^5$ is chloro; or $R^3$, $R^4$, and $R^6$ are ethyl and $R^5$ is chloro; or $R^3$, $R^4$, and $R^6$ are propyl and $R^5$ is chloro; or $R^3$, $R^4$, and $R^6$ are butyl and $R^5$ is chloro; or $R^3$, $R^5$, and $R^6$ are methyl and $R^4$ is chloro; or $R^3$, $R^5$, and $R^6$ are ethyl and $R^4$ is chloro; or $R^3$, $R^5$, and $R^6$ are propyl and $R^4$ is chloro; or $R^3$, $R^5$, and $R^6$ are butyl and $R^4$ is chloro; or $R^4$, $R^5$, and $R^6$ are methyl and $R^3$ is chloro; or $R^4$, $R^5$, and $R^6$ are ethyl and $R^3$ is chloro; or $R^4$, $R^5$, and $R^6$ are propyl and $R^3$ is chloro; or $R^4$, $R^5$, and $R^6$ are butyl and $R^3$ is chloro; or $R^3$, $R^4$, and $R^5$ are bromo and $R^6$ is methyl; or $R^3$, $R^4$, and $R^5$ are bromo and $R^6$ is ethyl; or $R^3$, $R^4$, and $R^5$ are bromo and $R^6$ is propyl; or $R^3$, $R^4$, and $R^5$ are bromo and $R^6$ is butyl; or $R^3$, $R^4$, and $R^6$ are bromo and $R^5$ is methyl; or $R^3$, $R^4$, and $R^6$ are bromo and $R^5$ is ethyl; or $R^3$, $R^4$, and $R^6$ are bromo and $R^5$ is propyl; or $R^3$, $R^4$, and $R^6$ are bromo and $R^5$ is butyl; or $R^3$, $R^5$, and $R^6$ are bromo and $R^4$ is methyl; or $R^3$, $R^5$, and $R^6$ are bromo and $R^4$ is ethyl; or $R^3$, $R^5$, and $R^6$ are bromo and $R^4$ is propyl; or $R^3$, $R^5$, and $R^6$ are bromo and $R^4$ is butyl; or $R^4$, $R^5$, and $R^6$ are bromo and $R^3$ is methyl; or $R^4$, $R^5$, and $R^6$ are bromo and $R^3$ is ethyl; or $R^4$, $R^5$, and $R^6$ are bromo and $R^3$ is propyl; or $R^4$, $R^5$, and $R^6$ are bromo and $R^3$ is butyl; or $R^3$ and $R^4$ are bromo and $R^5$ and $R^6$ are methyl; or $R^3$ and $R^5$ are bromo and $R^4$ and $R^6$ are methyl; or $R^3$ and $R^6$ are bromo and $R^4$ and $R^5$ are methyl; or $R^4$ and $R^5$ are bromo and $R^3$ and $R^6$ are methyl; or $R^4$ and $R^6$ are bromo and $R^3$ and $R^5$ are methyl; or $R^3$ and $R^4$ are bromo and $R^5$ and $R^6$ are ethyl; or $R^3$ and $R^5$ are bromo and $R^4$ and $R^6$ are ethyl; or $R^3$ and $R^6$ are bromo and $R^4$ and $R^5$ are ethyl; or $R^4$ and $R^5$ are bromo and $R^3$ and $R^6$ are ethyl; or $R^4$ and $R^6$ are bromo and $R^3$ and $R^5$ are ethyl; or $R^5$ and $R^6$ are bromo and $R^3$ and $R^4$ are ethyl; or $R^3$ and $R^4$ are bromo and $R^5$ and $R^6$ are propyl; or $R^3$ and $R^5$ are bromo and $R^4$ and $R^6$ are propyl; or $R^3$ and $R^6$ are bromo and $R^4$ and $R^5$ are propyl; or $R^4$ and $R^5$ are bromo and $R^3$ and $R^6$ are propyl; or $R^5$ and $R^6$ are bromo and $R^3$ and $R^4$ are propyl; or $R^3$ and $R^4$ are bromo and $R^5$ and $R^6$ are butyl; or $R^3$ and $R^5$ are bromo and $R^4$ and $R^6$ are butyl; or $R^3$ and $R^6$ are bromo and $R^4$ and $R^5$ are butyl; or $R^4$ and $R^5$ are bromo and $R^3$ and $R^6$ are butyl; or $R^4$ and $R^6$ are bromo and $R^3$ and $R^5$ are butyl; or $R^5$ and $R^6$ are bromo and $R^3$ and $R^4$ are butyl; or $R^3$, $R^4$, and $R^5$ are methyl and $R^6$ is bromo; or $R^3$, $R^4$, and $R^5$ are ethyl and $R^6$ is bromo; or $R^3$, $R^4$, and $R^5$ are propyl and $R^6$ is bromo; or $R^3$, $R^4$, and $R^5$ are butyl and $R^6$ is bromo; or $R^3$, $R^4$, and $R^6$ are methyl and $R^5$ is bromo; or $R^3$, $R^4$, and $R^6$ are ethyl and $R^5$ is bromo; or $R^3$, $R^4$, and $R^6$ are propyl and $R^5$ is bromo; or $R^3$, $R^4$, and $R^6$ are butyl and $R^5$ is bromo; or $R^3$, $R^5$, and $R^6$ are methyl and $R^4$ is bromo; or $R^3$, $R^5$, and $R^6$ are ethyl and $R^4$ is bromo; or $R^3$, $R^5$, and $R^6$ are propyl and $R^4$ is bromo; or $R^3$, $R^5$, and $R^6$ are butyl and $R^4$ is bromo; or $R^4$, $R^5$, and $R^6$ are methyl and $R^3$ is bromo; or $R^4$, $R^5$, and $R^6$ are ethyl and $R^3$ is bromo; or $R^4$, $R^5$, and $R^6$ are propyl and $R^3$ is bromo; or $R^4$, $R^5$, and $R^6$ are butyl and $R^3$ is bromo; or $R^3$, $R^4$, and $R^5$ are iodo and $R^6$ is methyl; or $R^3$, $R^4$, and $R^5$ are iodo and $R^6$ is ethyl; or $R^3$, $R^4$, and $R^5$ are iodo and $R^6$ is propyl; or $R^3$, $R^4$, and $R^5$ are iodo and $R^6$ is butyl; or $R^3$, $R^4$, and $R^6$ are iodo and $R^5$ is methyl; or $R^3$, $R^4$, and $R^6$ are iodo and $R^5$ is ethyl; or $R^3$, $R^4$, and $R^6$ are iodo and $R^5$ is propyl; or $R^3$, $R^4$, and $R^6$ are iodo and $R^5$ is butyl; or $R^3$, $R^5$, and $R^6$ are iodo and $R^4$ is methyl; or $R^3$, $R^5$, and $R^6$ are iodo and $R^4$ is ethyl; or $R^3$, $R^5$, and $R^6$ are iodo and $R^4$ is propyl; or $R^3$, $R^5$, and $R^6$ are iodo and $R^4$ is butyl; or $R^4$, $R^5$, and $R^6$ are iodo and $R^3$ is methyl; or $R^4$, $R^5$, and $R^6$ are iodo and $R^3$ is ethyl; or $R^4$, $R^5$, and $R^6$ are iodo and $R^3$ is propyl; or $R^4$, $R^5$, and $R^6$ are iodo and $R^3$ is butyl; or $R^3$ and $R^4$ are iodo and $R^5$ and $R^6$ are methyl; or $R^3$ and $R^5$ are iodo and $R^4$ and $R^6$ are methyl; or $R^3$ and $R^6$ are iodo and $R^4$ and $R^5$ are methyl; or $R^4$ and $R^5$ are iodo and $R^3$ and $R^6$ are methyl; or $R^4$ and $R^6$ are iodo and $R^3$ and $R^5$ are methyl; or $R^5$ and $R^6$ are iodo and $R^3$ and $R^4$ are methyl; or $R^3$ and $R^4$ are iodo and $R^5$ and $R^6$ are ethyl; or $R^3$ and $R^5$ are iodo and $R^4$ and $R^6$ are ethyl; or $R^3$ and $R^6$ are iodo and $R^4$ and $R^5$ are ethyl; or $R^4$ and $R^5$ are iodo and $R^3$ and $R^6$ are ethyl; or $R^4$ and $R^6$ are iodo and $R^3$ and $R^5$ are ethyl; or $R^5$ and $R^6$ are iodo and $R^3$ and $R^4$ are ethyl; or $R^3$ and $R^4$ are iodo and $R^5$ and $R^6$ are propyl; or $R^3$ and $R^5$ are iodo and $R^4$ and $R^6$ are propyl; or $R^3$ and $R^6$ are iodo and $R^4$ and $R^5$ are propyl; or $R^4$ and $R^5$ are iodo and $R^3$ and $R^6$ are propyl; or $R^4$ and $R^6$ are iodo and $R^3$ and $R^5$ are propyl; or $R^5$ and $R^6$ are iodo and $R^3$ and $R^4$ are propyl; or $R^3$ and $R^4$ are iodo and $R^5$ and $R^6$ are butyl; or $R^3$ and $R^5$ are iodo and $R^4$ and $R^6$ are butyl; or $R^3$ and $R^6$ are iodo and $R^4$ and $R^5$ are butyl; or $R^4$ and $R^5$ are iodo and $R^3$ and $R^6$ are butyl; or $R^4$ and $R^6$ are iodo and $R^3$ and $R^5$ are butyl; or $R^5$ and $R^6$ are iodo and $R^3$ and $R^4$ are butyl; or $R^3$, $R^4$, and $R^5$ are methyl and $R^6$ is iodo; or $R^3$, $R^4$, and $R^5$ are ethyl and $R^6$ is iodo; or $R^3$, $R^4$, and $R^5$ are propyl and $R^6$ is iodo; or $R^3$, $R^4$, and $R^5$ are butyl and $R^6$ is iodo; or $R^3$, $R^4$, and $R^6$ are methyl and $R^5$ is iodo; or $R^3$, $R^4$, and $R^6$ are ethyl and $R^5$ is iodo; or $R^3$, $R^4$, and $R^6$ are propyl and $R^5$ is iodo; or $R^3$, $R^4$, and $R^6$ are butyl and $R^5$ is iodo; or $R^3$, $R^5$, and $R^6$ are methyl and $R^4$ is iodo; or $R^3$, $R^5$, and $R^6$ are ethyl and $R^4$ is iodo; or $R^3$, $R^5$, and $R^6$ are propyl and $R^4$ is iodo; or $R^3$, $R^5$, and $R^6$ are butyl and $R^4$ is iodo; or $R^4$, $R^5$, and $R^6$ are methyl and $R^3$ is iodo; or $R^4$, $R^5$, and $R^6$ are ethyl and $R^3$ is iodo; or $R^4$, $R^5$, and $R^6$ are propyl and $R^3$ is iodo; or $R^4$, $R^5$, and $R^6$ are butyl and $R^3$ is iodo.

Alternatively, $R^3$, $R^4$, $R^5$, and $R^6$ may be comprised of halo and optionally substituted $C_{1-6}$-alkoxy, such as when $R^3$, $R^4$, and $R^5$ are fluoro and $R^6$ is methoxy; or $R^3$, $R^4$, and $R^5$ are fluoro and $R^6$ is ethoxy; or $R^3$, $R^4$, and $R^5$ are fluoro and $R^6$ is propoxy; or $R^3$, $R^4$, and $R^5$ are fluoro and $R^6$ is butoxy; or $R^3$, $R^4$, and $R^6$ are fluoro and $R^5$ is methoxy; or $R^3$, $R^4$, and $R^6$ are fluoro and $R^5$ is ethoxy; or $R^3$, $R^4$, and $R^6$ are fluoro and $R^5$ is propoxy; or $R^3$, $R^4$, and $R^6$ are fluoro and $R^5$ is butoxy; or $R^3$, $R^5$, and $R^6$ are fluoro and $R^4$ is methoxy; or $R^3$, $R^5$, and $R^6$ are fluoro and $R^4$ is ethoxy; or $R^3$, $R^5$, and $R^6$ are fluoro and $R^4$ is propoxy; or $R^3$, $R^5$, and $R^6$ are fluoro and $R^4$ is butoxy; or $R^4$, $R^5$, and $R^6$ are fluoro and $R^3$ is methoxy; or $R^4$, $R^5$, and $R^6$ are fluoro and $R^3$ is ethoxy; or $R^4$, $R^5$, and $R^6$ are fluoro and $R^3$ is propoxy; or $R^4$, $R^5$, and $R^6$ are fluoro and $R^3$ is butoxy; or $R^3$ and $R^4$ are fluoro and $R^5$ and $R^6$ are methoxy; or $R^3$ and $R^5$ are fluoro and $R^4$ and $R^6$ are methoxy; or $R^3$ and $R^6$ are fluoro and $R^4$ and $R^5$ are methoxy; or $R^4$ and $R^5$ are fluoro and $R^3$ and $R^6$ are methoxy; or $R^4$ and $R^6$ are fluoro and $R^3$ and $R^5$ are methoxy; or $R^5$ and $R^6$ are fluoro and $R^3$ and $R^4$ are methoxy; or $R^3$ and $R^4$ are fluoro and $R^5$ and $R^6$ are ethoxy; or $R^3$ and $R^5$ are fluoro and $R^4$ and $R^6$ are ethoxy; or $R^3$ and $R^6$ are fluoro and $R^4$ and $R^5$ are ethoxy; or $R^4$ and $R^5$ are fluoro and $R^3$ and $R^6$ are ethoxy; or $R^4$ and $R^6$ are fluoro and $R^3$ and $R^5$ are ethoxy; or $R^5$ and $R^6$ are fluoro and $R^3$ and $R^4$ are ethoxy; or $R^3$ and $R^4$ are fluoro and $R^5$ and $R^6$ are propoxy; or $R^3$ and $R^5$ are fluoro and $R^4$ and $R^6$ are propoxy; or $R^3$ and $R^6$ are fluoro and $R^4$ and $R^5$ are propoxy; or $R^4$ and $R^5$ are fluoro and $R^3$ and $R^6$ are propoxy; or $R^4$ and $R^6$ are fluoro and $R^3$ and $R^5$ are propoxy; or $R^5$ and $R^6$ are fluoro and $R^3$ and $R^4$ are propoxy; or $R^3$ and $R^4$ are fluoro and $R^5$ and $R^6$ are butoxy; or $R^3$ and $R^5$ are fluoro and $R^4$ and $R^6$ are butoxy; or $R^3$ and $R^6$ are fluoro and $R^4$ and $R^5$ are butoxy; or $R^4$ and $R^5$ are fluoro and $R^3$ and $R^6$ are butoxy; or $R^4$ and $R^6$ are fluoro and $R^3$ and $R^5$ are butoxy; or $R^5$ and $R^6$ are fluoro and $R^3$ and $R^4$ are butoxy; or $R^3$, $R^4$, and $R^5$ are methoxy and $R^6$ is fluoro; or $R^3$, $R^4$, and $R^5$ are ethoxy and $R^6$ is fluoro; or $R^3$, $R^4$, and $R^5$ are propoxy and $R^6$ is fluoro; or $R^3$, $R^4$, and $R^5$ are butoxy and $R^6$ is fluoro; or $R^3$, $R^4$, and $R^6$ are methoxy and $R^5$ is fluoro; or $R^3$, $R^4$, and $R^6$ are ethoxy and $R^5$ is fluoro; or $R^3$, $R^4$, and $R^6$ are propoxy and $R^5$ is fluoro; or $R^3$, $R^4$, and $R^6$ are butoxy and $R^5$ is fluoro; or $R^3$, $R^5$, and $R^6$ are methoxy and $R^4$ is fluoro; or $R^3$, $R^5$, and $R^6$ are ethoxy and $R^4$ is fluoro; or $R^3$, $R^5$, and $R^6$ are propoxy and $R^4$ is fluoro; or $R^3$, $R^5$, and $R^6$ are butoxy and $R^4$ is fluoro; or $R^4$, $R^5$, and $R^6$ are methoxy and $R^3$ is fluoro; or $R^4$, $R^5$, and $R^6$ are ethoxy and $R^3$ is fluoro; or $R^4$, $R^5$, and $R^6$ are propoxy and $R^3$ is fluoro; or $R^4$, $R^5$, and $R^6$ are butoxy and $R^3$ is fluoro; or $R^3$, $R^4$, and $R^5$ are chloro and $R^6$ is methoxy; or $R^3$, $R^4$, and $R^5$ are chloro and $R^6$ is ethoxy; or $R^3$, $R^4$, and $R^5$ are chloro and $R^6$ is propoxy; or $R^3$, $R^4$, and $R^5$ are chloro and $R^6$ is butoxy; or $R^3$, $R^4$, and $R^6$ are chloro and $R^5$ is methoxy; or $R^3$, $R^4$, and $R^6$ are chloro and $R^5$ is ethoxy; or $R^3$, $R^4$, and $R^6$ are chloro and $R^5$ is propoxy; or $R^3$, $R^4$, and $R^6$ are chloro and $R^5$ is butoxy; or $R^3$, $R^5$, and $R^6$ are chloro and $R^4$ is methoxy; or $R^3$, $R^5$, and $R^6$ are chloro and $R^4$ is ethoxy; or $R^3$, $R^5$, and $R^6$ are chloro and $R^4$ is propoxy; or $R^3$, $R^5$, and $R^6$ are chloro and $R^4$ is butoxy; or $R^4$, $R^5$, and $R^6$ are chloro and $R^3$ is methoxy; or $R^4$, $R^5$, and $R^6$ are chloro and $R^3$ is ethoxy; or $R^4$, $R^5$, and $R^6$ are chloro and $R^3$ is propoxy; or $R^4$, $R^5$, and $R^6$ are chloro and $R^3$ is butoxy; or $R^3$ and $R^4$ are chloro and $R^5$ and $R^6$ are methoxy; or $R^3$ and $R^5$ are chloro and $R^4$ and $R^6$ are methoxy; or $R^3$ and $R^6$ are chloro and $R^4$ and $R^5$ are methoxy; or $R^4$ and $R^5$ are chloro and $R^3$ and $R^6$ are methoxy; or $R^4$ and $R^6$ are chloro and $R^3$ and $R^5$ are methoxy; or $R^5$ and $R^6$ are chloro and $R^3$ and $R^4$ are methoxy; or $R^3$ and $R^4$ are chloro and $R^5$ and $R^6$ are ethoxy; or $R^3$ and $R^5$ are chloro and $R^4$ and $R^6$ are ethoxy; or $R^3$ and $R^6$ are chloro and $R^4$ and $R^5$ are ethoxy; or $R^4$ and $R^5$ are chloro and $R^3$ and $R^6$ are ethoxy; or $R^4$ and $R^6$ are chloro and $R^3$ and $R^5$ are ethoxy; or $R^5$ and $R^6$ are chloro and $R^3$ and $R^4$ are ethoxy; or $R^3$ and $R^4$ are chloro and $R^5$ and $R^6$ are propoxy; or $R^3$ and $R^5$ are chloro and $R^4$ and $R^6$ are propoxy; or $R^3$ and $R^6$ are chloro and $R^4$ and $R^5$ are propoxy; or $R^4$ and $R^5$ are chloro and $R^3$ and $R^6$ are propoxy; or $R^4$ and $R^6$ are chloro and $R^3$ and $R^5$ are propoxy; or $R^5$ and $R^6$ are chloro and $R^3$ and $R^4$ are propoxy; or $R^3$ and $R^4$ are chloro and $R^5$ and $R^6$ are butoxy; or $R^3$ and $R^5$ are chloro and $R^4$ and $R^6$ are butoxy; or $R^3$ and $R^6$ are chloro and $R^4$ and $R^5$ are butoxy; or $R^4$ and $R^5$ are chloro and $R^3$ and $R^6$ are butoxy; or $R^4$ and $R^6$ are chloro and $R^3$ and $R^5$ are butoxy; or $R^5$ and $R^6$ are chloro and $R^3$ and $R^4$ are butoxy; or $R^3$, $R^4$, and $R^5$ are methoxy and $R^6$ is chloro; or $R^3$, $R^4$, and $R^5$ are ethoxy and $R^6$ is chloro; or $R^3$, $R^4$, and $R^5$ are propoxy and $R^6$ is chloro; or $R^3$, $R^4$, and $R^5$ are butoxy and $R^6$ is chloro; or $R^3$, $R^4$, and $R^6$ are methoxy and $R^5$ is chloro; or $R^3$, $R^4$, and $R^6$ are ethoxy and $R^5$ is chloro; or $R^3$, $R^4$, and $R^6$ are propoxy and $R^5$ is chloro; or $R^3$, $R^4$, and $R^6$ are butoxy and $R^5$ is chloro; or $R^3$, $R^5$, and $R^6$ are methoxy and $R^4$ is chloro; or $R^3$, $R^5$, and $R^6$ are ethoxy and $R^4$ is chloro; or $R^3$, $R^5$, and $R^6$ are propoxy and $R^4$ is chloro; or $R^3$, $R^5$, and $R^6$ are butoxy and $R^4$ is chloro; or $R^4$, $R^5$, and $R^6$ are methoxy and $R^3$ is chloro; or $R^4$, $R^5$, and $R^6$ are ethoxy and $R^3$ is chloro; or $R^4$, $R^5$, and $R^6$ are propoxy and $R^3$ is chloro; or $R^4$, $R^5$, and $R^6$ are butoxy and $R^3$ is chloro; or $R^3$, $R^4$, and $R^5$ are bromo and $R^6$ is methoxy; or $R^3$, $R^4$, and $R^5$ are bromo and $R^6$ is ethoxy; or $R^3$, $R^4$, and $R^5$ are bromo and $R^6$ is propoxy; or $R^3$, $R^4$, and $R^5$ are bromo and $R^6$ is butoxy; or $R^3$, $R^4$, and $R^6$ are bromo and $R^5$ is methoxy; or $R^3$, $R^4$, and $R^6$ are bromo and $R^5$ is ethoxy; or $R^3$, $R^4$, and $R^6$ are bromo and $R^5$ is propoxy; or $R^3$, $R^4$, and $R^6$ are bromo and $R^5$ is butoxy; or $R^3$, $R^5$, and $R^6$ are bromo and $R^4$ is methoxy; or $R^3$, $R^5$, and $R^6$ are bromo and $R^4$ is ethoxy; or $R^3$, $R^5$, and $R^6$ are bromo and $R^4$ is propoxy; or $R^3$, $R^5$, and $R^6$ are bromo and $R^4$ is butoxy; or $R^4$, $R^5$, and $R^6$ are bromo and $R^3$ is methoxy; or $R^4$, $R^5$, and $R^6$ are bromo and $R^3$ is ethoxy; or $R^4$, $R^5$, and $R^6$ are bromo and $R^3$ is propoxy; or $R^4$, $R^5$, and $R^6$ are bromo and $R^3$ is butoxy; or $R^3$ and $R^4$ are bromo and $R^5$ and $R^6$ are methoxy; or $R^3$ and $R^5$ are bromo and $R^4$ and $R^6$ are methoxy; or $R^3$ and $R^6$ are bromo and $R^4$ and $R^5$ are methoxy; or $R^4$ and $R^5$ are bromo and $R^3$ and $R^6$ are methoxy; or $R^4$ and $R^6$ are bromo and $R^3$ and $R^5$ are methoxy; or $R^5$ and $R^6$ are bromo and $R^3$ and $R^4$ are methoxy; or $R^3$ and $R^4$ are bromo and $R^5$ and $R^6$ are ethoxy; or $R^3$ and $R^5$ are bromo and $R^4$ and $R^6$ are ethoxy; or $R^3$ and $R^6$ are bromo and $R^4$ and $R^5$ are ethoxy; or $R^4$ and $R^5$ are bromo and $R^3$ and $R^6$ are ethoxy; or $R^4$ and $R^6$ are bromo and $R^3$ and $R^5$ are ethoxy; or $R^5$ and $R^6$ are bromo and $R^3$ and $R^4$ are ethoxy; or $R^3$ and $R^4$ are bromo and $R^5$ and $R^6$ are propoxy; or $R^3$ and $R^5$ are bromo and $R^4$ and $R^6$ are propoxy; or $R^3$ and $R^6$ are bromo and $R^4$ and $R^5$ are propoxy; or $R^4$ and $R^5$ are bromo and $R^3$ and $R^6$ are propoxy; or $R^4$ and $R^6$ are bromo and $R^3$ and $R^5$ are propoxy; or $R^5$ and $R^6$ are bromo and $R^3$ and $R^4$ are propoxy; or $R^3$ and $R^4$ are bromo and $R^5$ and $R^6$ are butoxy; or $R^3$ and $R^5$ are bromo and $R^4$ and $R^6$ are butoxy; or $R^3$ and $R^6$ are bromo and $R^4$ and $R^5$ are butoxy; or $R^4$ and $R^5$ are bromo and $R^3$ and $R^6$ are butoxy; or $R^4$ and $R^6$ are bromo and $R^3$ and $R^5$ are butoxy; or $R^5$ and $R^6$ are bromo and $R^3$ and $R^4$ are butoxy; or $R^3$, $R^4$, and $R^5$ are methoxy and $R^6$ is bromo; or $R^3$, $R^4$, and $R^5$ are ethoxy and $R^6$ is bromo; or $R^3$, $R^4$, and $R^5$ are propoxy and $R^6$ is bromo; or $R^3$, $R^4$, and $R^5$ are butoxy and $R^6$ is bromo; or $R^3$, $R^4$, and $R^6$ are methoxy and $R^5$ is bromo; or $R^3$, $R^4$, and $R^6$ are ethoxy and $R^5$ is bromo; or $R^3$, $R^4$, and $R^6$ are propoxy and $R^5$ is bromo; or $R^3$, $R^4$, and $R^6$ are butoxy and $R^5$ is bromo; or $R^3$, $R^5$, and $R^6$ are methoxy and $R^4$ is bromo; or $R^3$, $R^5$, and $R^6$ are ethoxy and $R^4$ is bromo; or $R^3$, $R^5$, and $R^6$ are propoxy and $R^4$ is bromo; or $R^3$, $R^5$, and $R^6$ are butoxy and $R^4$ is bromo; or $R^4$, $R^5$, and $R^6$ are methoxy and $R^3$ is bromo; or $R^4$, $R^5$, and $R^6$ are ethoxy and $R^3$ is bromo; or $R^4$, $R^5$, and $R^6$ are propoxy and $R^3$ is bromo; or $R^4$, $R^5$, and $R^6$ are butoxy and $R^3$ is bromo; or $R^3$, $R^4$, and $R^5$ are iodo and $R^6$ is methoxy; or $R^3$, $R^4$, and $R^5$ are iodo and $R^6$ is ethoxy; or $R^3$, $R^4$, and $R^5$ are iodo and $R^6$ is propoxy; or $R^3$, $R^4$, and $R^5$ are iodo and $R^6$ is butoxy; or $R^3$, $R^4$, and $R^6$ are iodo and $R^5$ is methoxy; or $R^3$, $R^4$, and $R^6$ are iodo and $R^5$ is ethoxy; or $R^3$, $R^4$, and $R^6$ are iodo and $R^5$ is propoxy; or $R^3$, $R^4$, and $R^6$ are iodo and $R^5$ is butoxy; or $R^3$, $R^5$, and $R^6$ are iodo and $R^4$ is methoxy; or $R^3$, $R^5$, and $R^6$ are iodo and $R^4$ is ethoxy; or $R^3$, $R^5$, and $R^6$ are iodo and $R^4$ is propoxy; or $R^3$, $R^5$, and $R^6$ are iodo and $R^4$ is butoxy; or $R^4$, $R^5$, and $R^6$ are iodo and $R^3$ is methoxy; or $R^4$, $R^5$, and $R^6$ are iodo and $R^3$ is ethoxy; or $R^4$, $R^5$, and $R^6$ are iodo and $R^3$ is propoxy; or $R^4$, $R^5$, and $R^6$ are iodo and $R^3$ is butoxy; or $R^3$ and $R^4$ are iodo and $R^5$ and $R^6$ are methoxy; or $R^3$ and $R^5$ are iodo and $R^4$ and $R^6$ are methoxy; or $R^3$ and $R^6$ are iodo and $R^4$ and $R^5$ are methoxy; or $R^4$ and $R^5$ are iodo and $R^3$ and $R^6$ are methoxy; or $R^4$ and $R^6$ are iodo and $R^3$ and $R^5$ are methoxy; or $R^5$ and $R^6$ are iodo and $R^3$ and $R^4$ are methoxy; or $R^3$ and $R^4$ are iodo and $R^5$ and $R^6$ are ethoxy; or $R^3$ and $R^5$ are iodo and $R^4$ and $R^6$ are ethoxy; or $R^3$ and $R^6$ are iodo and $R^4$ and $R^5$ are ethoxy; or $R^4$ and $R^5$ are iodo and $R^3$ and $R^6$ are ethoxy; or $R^4$ and $R^6$ are iodo and $R^3$ and $R^5$ are ethoxy; or $R^5$ and $R^6$ are iodo and $R^3$ and $R^4$ are ethoxy; or $R^3$ and $R^4$ are iodo and $R^5$ and $R^6$ are propoxy; or $R^3$ and $R^5$ are iodo and $R^4$ and $R^6$ are propoxy; or $R^3$ and $R^6$ are iodo and $R^4$ and $R^5$ are propoxy; or $R^4$ and $R^5$ are iodo and $R^3$ and $R^6$ are propoxy; or $R^4$ and $R^6$ are iodo and $R^3$ and $R^5$ are propoxy; or $R^5$ and $R^6$ are iodo and $R^3$ and $R^4$ are propoxy; or $R^3$ and $R^4$ are iodo and $R^5$ and $R^6$ are butoxy; or $R^3$ and $R^5$ are iodo and $R^4$ and $R^6$ are butoxy; or $R^3$ and $R^6$ are iodo and $R^4$ and $R^5$ are butoxy; or $R^4$ and $R^5$ are iodo and $R^3$ and $R^6$ are butoxy; or $R^4$ and $R^6$ are iodo and $R^3$ and $R^5$ are butoxy; or $R^5$ and $R^6$ are iodo and $R^3$ and $R^4$ are butoxy; or $R^3$, $R^4$, and $R^5$ are methoxy and $R^6$ is iodo; or $R^3$, $R^4$, and $R^5$ are ethoxy and $R^6$ is iodo; or $R^3$, $R^4$, and $R^5$ are propoxy and $R^6$ is iodo; or $R^3$, $R^4$, and $R^5$ are butoxy and $R^6$ is iodo; or $R^3$, $R^4$, and $R^6$ are methoxy and $R^5$ is iodo; or $R^3$, $R^4$, and $R^6$ are ethoxy and $R^5$ is iodo; or $R^3$, $R^4$, and $R^6$ are propoxy and $R^5$ is iodo; or $R^3$, $R^4$, and $R^6$ are butoxy and $R^5$ is iodo; or $R^3$, $R^5$, and $R^6$ are methoxy and $R^4$ is iodo; or $R^3$, $R^5$, and $R^6$ are ethoxy and $R^4$ is iodo; or $R^3$, $R^5$, and $R^6$ are propoxy and $R^4$ is iodo; or $R^3$, $R^5$, and $R^6$ are butoxy and $R^4$ is iodo; or $R^4$, $R^5$, and $R^6$ are methoxy and $R^3$ is iodo; or $R^4$, $R^5$, and $R^6$ are ethoxy and $R^3$ is iodo; or $R^4$, $R^5$, and $R^6$ are propoxy and $R^3$ is iodo; or $R^4$, $R^5$, and $R^6$ are butoxy and $R^3$ is iodo.

Alternatively, $R^3$, $R^4$, $R^5$, and $R^6$ may be comprised of optionally substituted $C_{1-6}$-alkyl and optionally substituted $C_{1-6}$-alkoxy, such as when $R^3$, $R^4$, and $R^5$ are methyl and $R^6$ is methoxy; or $R^3$, $R^4$, and $R^5$ are methyl and $R^6$ is ethoxy; or $R^3$, $R^4$, and $R^5$ are methyl and $R^6$ is propoxy; or $R^3$, $R^4$, and $R^5$ are methyl and $R^6$ is butoxy; or $R^3$, $R^4$, and $R^6$ are methyl and $R^5$ is methoxy; or $R^3$, $R^4$, and $R^6$ are methyl and $R^5$ is ethoxy; or $R^3$, $R^4$, and $R^6$ are methyl and $R^5$ is propoxy; or $R^3$, $R^4$, and $R^6$ are methyl and $R^5$ is butoxy; or $R^3$, $R^5$, and $R^6$ are methyl and $R^4$ is methoxy; or $R^3$, $R^5$, and $R^6$ are methyl and $R^4$ is ethoxy; or $R^3$, $R^5$, and $R^6$ are methyl and $R^4$ is propoxy; or $R^3$, $R^5$, and $R^6$ are methyl and $R^4$ is butoxy; or $R^4$, $R^5$, and $R^6$ are methyl and $R^3$ is methoxy; or $R^4$, $R^5$, and $R^6$ are methyl and $R^3$ is ethoxy; or $R^4$, $R^5$, and $R^6$ are methyl and $R^3$ is propoxy; or $R^4$, $R^5$, and $R^6$ are methyl and $R^3$ is butoxy; or $R^3$ and $R^4$ are methyl and $R^5$ and $R^6$ are methoxy; or $R^3$ and $R^5$ are methyl and $R^4$ and $R^6$ are methoxy; or $R^3$ and $R^6$ are methyl and $R^4$ and $R^5$ are methoxy; or $R^4$ and $R^5$ are methyl and $R^3$ and $R^6$ are methoxy; or $R^4$ and $R^6$ are methyl and $R^3$ and $R^5$ are methoxy; or $R^5$ and $R^6$ are methyl and $R^3$ and $R^4$ are methoxy; or $R^3$ and $R^4$ are methyl and $R^5$ and $R^6$ are ethoxy; or $R^3$ and $R^5$ are methyl and $R^4$ and $R^6$ are ethoxy; or $R^3$ and $R^6$ are methyl and $R^4$ and $R^5$ are ethoxy; or $R^4$ and $R^5$ are methyl and $R^3$ and $R^6$ are ethoxy; or $R^4$ and $R^6$ are methyl and $R^3$ and $R^5$ are ethoxy; or $R^5$ and $R^6$ are methyl and $R^3$ and $R^4$ are ethoxy; or $R^3$ and $R^4$ are methyl and $R^5$ and $R^6$ are propoxy; or $R^3$ and $R^5$ are methyl and $R^4$ and $R^6$ are propoxy; or $R^3$ and $R^6$ are methyl and $R^4$ and $R^5$ are propoxy; or $R^4$ and $R^5$ are methyl and $R^3$ and $R^6$ are propoxy; or $R^4$ and $R^6$ are methyl and $R^3$ and $R^5$ are propoxy; or $R^5$ and $R^6$ are methyl and $R^3$ and $R^4$ are propoxy; or $R^3$ and $R^4$ are methyl and $R^5$ and $R^6$ are butoxy; or $R^3$ and $R^5$ are methyl and $R^4$ and $R^6$ are butoxy; or $R^3$ and $R^6$ are methyl and $R^4$ and $R^5$ are butoxy; or $R^4$ and $R^5$ are methyl and $R^3$ and $R^6$ are butoxy; or $R^4$ and $R^6$ are methyl and $R^3$ and $R^5$ are butoxy; or $R^5$ and $R^6$ are methyl and $R^3$ and $R^4$ are butoxy; or $R^3$, $R^4$, and $R^5$ are methoxy and $R^6$ is methyl; or $R^3$, $R^4$, and $R^5$ are ethoxy and $R^6$ is methyl; or $R^3$, $R^4$, and $R^5$ are propoxy and $R^6$ is methyl; or $R^3$, $R^4$, and $R^5$ are butoxy and $R^6$ is methyl; or $R^3$, $R^4$, and $R^6$ are methoxy and $R^5$ is methyl; or $R^3$, $R^4$, and $R^6$ are ethoxy and $R^5$ is methyl; or $R^3$, $R^4$, and $R^6$ are propoxy and $R^5$ is methyl; or $R^3$, $R^4$, and $R^6$ are butoxy and $R^5$ is methyl; or $R^3$, $R^5$, and $R^6$ are methoxy and $R^4$ is methyl; or $R^3$, $R^5$, and $R^6$ are ethoxy and $R^4$ is methyl; or $R^3$, $R^5$, and $R^6$ are propoxy and $R^4$ is methyl; or $R^3$, $R^5$, and $R^6$ are butoxy and $R^4$ is methyl; or $R^4$, $R^5$, and $R^6$ are methoxy and $R^3$ is methyl; or $R^4$, $R^5$, and $R^6$ are ethoxy and $R^3$ is methyl; or $R^4$, $R^5$, and $R^6$ are propoxy and $R^3$ is methyl; or $R^4$, $R^5$, and $R^6$ are butoxy and $R^3$ is methyl; or $R^3$, $R^4$, and $R^5$ are ethyl and $R^6$ is methoxy; or $R^3$, $R^4$, and $R^5$ are ethyl and $R^6$ is ethoxy; or $R^3$, $R^4$, and $R^5$ are ethyl and $R^6$ is propoxy; or $R^3$, $R^4$, and $R^5$ are ethyl and $R^6$ is butoxy; or $R^3$, $R^4$, and $R^6$ are ethyl and $R^5$ is methoxy; or $R^3$, $R^4$, and $R^6$ are ethyl and $R^5$ is ethoxy; or $R^3$, $R^4$, and $R^6$ are ethyl and $R^5$ is propoxy; or $R^3$, $R^4$, and $R^6$ are ethyl and $R^5$ is butoxy; or $R^3$, $R^5$, and $R^6$ are ethyl and $R^4$ is methoxy; or $R^3$, $R^5$, and $R^6$ are ethyl and $R^4$ is ethoxy; or $R^3$, $R^5$, and $R^6$ are ethyl and $R^4$ is propoxy; or $R^3$, $R^5$, and $R^6$ are ethyl and $R^4$ is butoxy; or $R^4$, $R^5$, and $R^6$ are ethyl and $R^3$ is methoxy; or $R^4$, $R^5$, and $R^6$ are ethyl and $R^3$ is ethoxy; or $R^4$, $R^5$, and $R^6$ are ethyl and $R^3$ is propoxy; or $R^4$, $R^5$, and $R^6$ are ethyl and $R^3$ is butoxy; or $R^3$ and $R^4$ are ethyl and $R^5$ and $R^6$ are methoxy; or $R^3$ and $R^5$ are ethyl and $R^4$ and $R^6$ are methoxy; or $R^3$ and $R^6$ are ethyl and $R^4$ and $R^5$ are methoxy; or $R^4$ and $R^5$ are ethyl and $R^3$ and $R^6$ are methoxy; or $R^4$ and $R^6$ are ethyl and $R^3$ and $R^5$ are methoxy; or $R^5$ and $R^6$ are ethyl and $R^3$ and $R^4$ are methoxy; or $R^3$ and $R^4$ are ethyl and $R^5$ and $R^6$ are ethoxy; or $R^3$ and $R^5$ are ethyl and $R^4$ and $R^6$ are ethoxy; or $R^3$ and $R^6$ are ethyl and $R^4$ and $R^5$ are ethoxy; or $R^4$ and $R^5$ are ethyl and $R^3$ and $R^6$ are ethoxy; or $R^4$ and $R^6$ are ethyl and $R^3$ and $R^5$ are ethoxy; or $R^5$ and $R^6$ are ethyl and $R^3$ and $R^4$ are ethoxy; or $R^3$ and $R^4$ are ethyl and $R^5$ and $R^6$ are propoxy; or $R^3$ and $R^5$ are ethyl and $R^4$ and $R^6$ are propoxy; or $R^3$ and $R^6$ are ethyl and $R^4$ and $R^5$ are propoxy; or $R^4$ and $R^5$ are ethyl and $R^3$ and $R^6$ are propoxy; or $R^4$ and $R^6$ are ethyl and $R^3$ and $R^5$ are propoxy; or $R^5$ and $R^6$ are ethyl and $R^3$ and $R^4$ are propoxy; or $R^3$ and $R^4$ are ethyl and $R^5$ and $R^6$ are butoxy; or $R^3$ and $R^5$ are ethyl and $R^4$ and $R^6$ are butoxy; or $R^3$ and $R^6$ are ethyl and $R^4$ and $R^5$ are butoxy; or $R^4$ and $R^5$ are ethyl and $R^3$ and $R^6$ are butoxy; or $R^4$ and $R^6$ are ethyl and $R^3$ and $R^5$ are butoxy; or $R^5$ and $R^6$ are ethyl and $R^3$ and $R^4$ are butoxy; or $R^3$, $R^4$, and $R^5$ are methoxy and $R^6$ is ethyl; or $R^3$, $R^4$, and $R^5$ are ethoxy and $R^6$ is ethyl; or $R^3$, $R^4$, and $R^5$ are propoxy and $R^6$ is ethyl; or $R^3$, $R^4$, and $R^5$ are butoxy and $R^6$ is ethyl; or $R^3$, $R^4$, and $R^6$ are methoxy and $R^5$ is ethyl; or $R^3$, $R^4$, and $R^6$ are ethoxy and $R^5$ is ethyl; or $R^3$, $R^4$, and $R^6$ are propoxy and $R^5$ is ethyl; or $R^3$, $R^4$, and $R^6$ are butoxy and $R^5$ is ethyl; or $R^3$, $R^5$, and $R^6$ are methoxy and $R^4$ is ethyl; or $R^3$, $R^5$, and $R^6$ are ethoxy and $R^4$ is ethyl; or $R^3$, $R^5$, and $R^6$ are propoxy and $R^4$ is ethyl; or $R^3$, $R^5$, and $R^6$ are butoxy and $R^4$ is ethyl; or $R^4$, $R^5$, and $R^6$ are methoxy and $R^3$ is ethyl; or $R^4$, $R^5$, and $R^6$ are ethoxy and $R^3$ is ethyl; or $R^4$, $R^5$, and $R^6$ are propoxy and $R^3$ is ethyl; or $R^4$, $R^5$, and $R^6$ are butoxy and $R^3$ is ethyl; or $R^3$, $R^4$, and $R^5$ are propyl and $R^6$ is methoxy; or $R^3$, $R^4$, and $R^5$ are propyl and $R^6$ is ethoxy; or $R^3$, $R^4$, and $R^5$ are propyl and $R^6$ is propoxy; or $R^3$, $R^4$, and $R^5$ are propyl and $R^6$ is butoxy; or $R^3$, $R^4$, and $R^6$ are propyl and $R^5$ is methoxy; or $R^3$, $R^4$, and $R^6$ are propyl and $R^5$ is ethoxy; or $R^3$, $R^4$, and $R^6$ are propyl and $R^5$ is propoxy; or $R^3$, $R^4$, and $R^6$ are propyl and $R^5$ is butoxy; or $R^3$, $R^5$, and $R^6$ are propyl and $R^4$ is methoxy; or $R^3$, $R^5$, and $R^6$ are propyl and $R^4$ is ethoxy; or $R^3$, $R^5$, and $R^6$ are propyl and $R^4$ is propoxy; or $R^3$, $R^5$, and $R^6$ are propyl and $R^4$ is butoxy; or $R^4$, $R^5$, and $R^6$ are propyl and $R^3$ is methoxy; or $R^4$, $R^5$, and $R^6$ are propyl and $R^3$ is ethoxy; or $R^4$, $R^5$, and $R^6$ are propyl and $R^3$ is propoxy; or $R^4$, $R^5$, and $R^6$ are propyl and $R^3$ is butoxy; or $R^3$ and $R^4$ are propyl and $R^5$ and $R^6$ are methoxy; or $R^3$ and $R^5$ are propyl and $R^4$ and $R^6$ are methoxy; or $R^3$ and $R^6$ are propyl and $R^4$ and $R^5$ are methoxy; or $R^4$ and $R^5$ are propyl and $R^3$ and $R^6$ are methoxy; or $R^4$ and $R^6$ are propyl and $R^3$ and $R^5$ are methoxy; or $R^5$ and $R^6$ are propyl and $R^3$ and $R^4$ are methoxy; or $R^3$ and $R^4$ are propyl and $R^5$ and $R^6$ are ethoxy; or $R^3$ and $R^5$ are propyl and $R^4$ and $R^6$ are ethoxy; or $R^3$ and $R^6$ are propyl and $R^4$ and $R^5$ are ethoxy; or $R^4$ and $R^5$ are propyl and $R^3$ and $R^6$ are ethoxy; or $R^4$ and $R^6$ are propyl and $R^3$ and $R^5$ are ethoxy; or $R^5$ and $R^6$ are propyl and $R^3$ and $R^4$ are ethoxy; or $R^3$ and $R^4$ are propyl and $R^5$ and $R^6$ are propoxy; or $R^3$ and $R^5$ are propyl and $R^4$ and $R^6$ are propoxy; or $R^3$ and $R^6$ are propyl and $R^4$ and $R^5$ are propoxy; or $R^4$ and $R^5$ are propyl and $R^3$ and $R^6$ are propoxy; or $R^4$ and $R^6$ are propyl and $R^3$ and $R^5$ are propoxy; or $R^5$ and $R^6$ are propyl and $R^3$ and $R^4$ are propoxy; or $R^3$ and $R^4$ are propyl and $R^5$ and $R^6$ are butoxy; or $R^3$ and $R^5$ are propyl and $R^4$ and $R^6$ are butoxy; or $R^3$ and $R^6$ are propyl and $R^4$ and $R^5$ are butoxy; or $R^4$ and $R^5$ are propyl and $R^3$ and $R^6$ are butoxy; or $R^4$ and $R^6$ are propyl and $R^3$ and $R^5$ are butoxy; or $R^5$ and $R^6$ are propyl and $R^3$ and $R^4$ are butoxy; or $R^3$, $R^4$, and $R^5$ are methoxy and $R^6$ is propyl; or $R^3$, $R^4$, and $R^5$ are ethoxy and $R^6$ is propyl; or $R^3$, $R^4$, and $R^5$ are propoxy and $R^6$ is propyl; or $R^3$, $R^4$, and $R^5$ are butoxy and $R^6$ is propyl; or $R^3$, $R^4$, and $R^6$ are methoxy and $R^5$ is propyl; or $R^3$, $R^4$, and $R^6$ are ethoxy and $R^5$ is propyl; or $R^3$, $R^4$, and $R^6$ are propoxy and $R^5$ is propyl; or $R^3$, $R^4$, and $R^6$ are butoxy and $R^5$ is propyl; or $R^3$, $R^5$, and $R^6$ are methoxy and $R^4$ is propyl; or $R^3$, $R^5$, and $R^6$ are ethoxy and $R^4$ is propyl; or $R^3$, $R^5$, and $R^6$ are propoxy and $R^4$ is propyl; or $R^3$, $R^5$, and $R^6$ are butoxy and $R^4$ is propyl; or $R^4$, $R^5$, and $R^6$ are methoxy and $R^3$ is propyl; or $R^4$, $R^5$, and $R^6$ are ethoxy and $R^3$ is propyl; or $R^4$, $R^5$, and $R^6$ are propoxy and $R^3$ is propyl; or $R^4$, $R^5$, and $R^6$ are butoxy and $R^3$ is propyl; or $R^3$, $R^4$, and $R^5$ are butyl and $R^6$ is methoxy; or $R^3$, $R^4$, and $R^5$ are butyl and $R^6$ is ethoxy; or $R^3$, $R^4$, and $R^5$ are butyl and $R^6$ is propoxy; or $R^3$, $R^4$, and $R^5$ are butyl and $R^6$ is butoxy; or $R^3$, $R^4$, and $R^6$ are butyl and $R^5$ is methoxy; or $R^3$, $R^4$, and $R^6$ are butyl and $R^5$ is ethoxy; or $R^3$, $R^4$, and $R^6$ are butyl and $R^5$ is propoxy; or $R^3$, $R^4$, and $R^6$ are butyl and $R^5$ is butoxy; or $R^3$, $R^5$, and $R^6$ are butyl and $R^4$ is methoxy; or $R^3$, $R^5$, and $R^6$ are butyl and $R^4$ is ethoxy; or $R^3$, $R^5$, and $R^6$ are butyl and $R^4$ is propoxy; or $R^3$, $R^5$, and $R^6$ are butyl and $R^4$ is butoxy; or $R^4$, $R^5$, and $R^6$ are butyl and $R^3$ is methoxy; or $R^4$, $R^5$, and $R^6$ are butyl and $R^3$ is ethoxy; or $R^4$, $R^5$, and $R^6$ are butyl and $R^3$ is propoxy; or $R^4$, $R^5$, and $R^6$ are butyl and $R^3$ is butoxy; or $R^3$ and $R^4$ are butyl and $R^5$ and $R^6$ are methoxy; or $R^3$ and $R^5$ are butyl and $R^4$ and $R^6$ are methoxy; or $R^3$ and $R^6$ are butyl and $R^4$ and $R^5$ are methoxy; or $R^4$ and $R^5$ are butyl and $R^3$ and $R^6$ are methoxy; or $R^4$ and $R^6$ are butyl and $R^3$ and $R^5$ are methoxy; or $R^5$ and $R^6$ are butyl and $R^3$ and $R^4$ are methoxy; or $R^3$ and $R^4$ are butyl and $R^5$ and $R^6$ are ethoxy; or $R^3$ and $R^5$ are butyl and $R^4$ and $R^6$ are ethoxy; or $R^3$ and $R^6$ are butyl and $R^4$ and $R^5$ are ethoxy; or $R^4$ and $R^5$ are butyl and $R^3$ and $R^6$ are ethoxy; or $R^4$ and $R^6$ are butyl and $R^3$ and $R^5$ are ethoxy; or $R^5$ and $R^6$ are butyl and $R^3$ and $R^4$ are ethoxy; or $R^3$ and $R^4$ are butyl and $R^5$ and $R^6$ are propoxy; or $R^3$ and $R^5$ are butyl and $R^4$ and $R^6$ are propoxy; or $R^3$ and $R^6$ are butyl and $R^4$ and $R^5$ are propoxy; or $R^4$ and $R^5$ are butyl and $R^3$ and $R^6$ are propoxy; or $R^4$ and $R^6$ are butyl and $R^3$ and $R^5$ are propoxy; or $R^5$ and $R^6$ are butyl and $R^3$ and $R^4$ are propoxy; or $R^3$ and $R^4$ are butyl and $R^5$ and $R^6$ are butoxy; or $R^3$ and $R^5$ are butyl and $R^4$ and $R^6$ are butoxy; or $R^3$ and $R^6$ are butyl and $R^4$ and $R^5$ are butoxy; or $R^4$ and $R^5$ are butyl and $R^3$ and $R^6$ are butoxy; or $R^4$ and $R^6$ are butyl and $R^3$ and $R^5$ are butoxy; or $R^5$ and $R^6$ are butyl and $R^3$ and $R^4$ are butoxy; or $R^3$, $R^4$, and $R^5$ are methoxy and $R^6$ is butyl; or $R^3$, $R^4$, and $R^5$ are ethoxy and $R^6$ is butyl; or $R^3$, $R^4$, and $R^5$ are propoxy and $R^6$ is butyl; or $R^3$, $R^4$, and $R^5$ are butoxy and $R^6$ is butyl; or $R^3$, $R^4$, and $R^6$ are methoxy and $R^5$ is butyl; or $R^3$, $R^4$, and $R^6$ are ethoxy and $R^5$ is butyl; or $R^3$, $R^4$, and $R^6$ are propoxy and $R^5$ is butyl; or $R^3$, $R^4$, and $R^6$ are butoxy and $R^5$ is butyl; or $R^3$, $R^5$, and $R^6$ are methoxy and $R^4$ is butyl; or $R^3$, $R^5$, and $R^6$ are ethoxy and $R^4$ is butyl; or $R^3$, $R^5$, and $R^6$ are propoxy and $R^4$ is butyl; or $R^3$, $R^5$, and $R^6$ are butoxy and $R^4$ is butyl; or $R^4$, $R^5$, and $R^6$ are methoxy and $R^3$ is butyl; or $R^4$, $R^5$, and $R^6$ are ethoxy and $R^3$ is butyl; or $R^4$, $R^5$, and $R^6$ are propoxy and $R^3$ is butyl; or $R^4$, $R^5$, and $R^6$ are butoxy and $R^3$ is butyl.

As stated above, $R^7$ is a phosphorus containing moiety, wherein a phosphorus atom is bonded to Au. The phosphorus-containing moiety is not particularly limited, except that a phosphorus atom of the phosphorus-containing moiety is bonded directly to the Au(I) ion. As such, the phosphorus containing moiety could contain more than one phosphorus atom, as long as the gold(I) is bonded to one of them. As one of skill in the art will appreciate, the nature of the phosphorus containing moiety could affect the stability of the resulting compound.

In one embodiment, $R^7$ may be a moiety of the type:

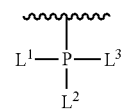

wherein $L^1$, $L^2$, and $L^3$ are each independently selected from optionally substituted aryl or optionally substituted heteroaryl; or two or more of $L^1$, $L^2$, or $L^3$, when taken together with the phosphorus atom to which they are attached, form an optionally substituted heterocyclic moiety.

When $R^3$, $R^4$, $R^5$, and $R^6$ are H, and $R^1$ and $R^2$ are phenyl and $R^7$ is a moiety of the type described above the invention provides a compound of Formula (IV):

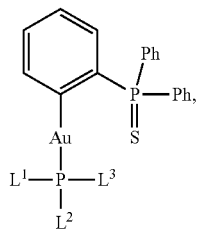

(IV)

wherein $L^1$, $L^2$ and $L^3$ are as defined herein.

In one embodiment $R^5$, and $R^6$ are H, and $R^1$ and $R^2$ are phenyl and $R^7$ is a moiety of the type described above and the invention provides a compound of Formula (IVa):

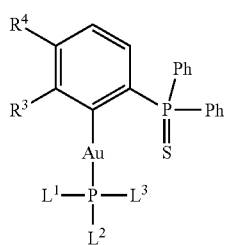

(IVa)

wherein $R^3$, $R^4$, $L^1$, $L^2$ and $L^3$ are as defined herein.

The phosphorus atom which is bonded directly to the gold atom is typically attached to three other atoms/groups. As stated above $L^1$, $L^2$, and $L^3$ are each independently selected from optionally substituted aryl or optionally substituted heteroaryl; or two or more of $L^1$, $L^2$, or $L^3$, when taken together with the phosphorus atom to which they are attached, form an optionally substituted heterocyclic moiety.

In some embodiments the groups, $L^1$, $L^2$, and $L^3$ may be optionally substituted aryl or optionally substituted heteroaryl. Examples of aryl are phenyl and naphthyl, preferably phenyl. It is not intended to limit the invention by the number of groups which are optionally substituted onto the aryl, nor the positions of the optional substituents about the aryl. For example, in one embodiment, phenyl is substituted with a sulfonate group. The sulfonate, a derivative of sulfonic acid, can be a sulfonate ester such as a methyl ester or an ethyl ester, or it could have a counter-ion. Examples of counter-ions include sodium and potassium. In one preferred embodiment, the counter-ion is sodium. The sulfonate could be substituted at any position on the phenyl ring, relative to the phosphorus atom. For example, the optionally substituted aryl may be 2-phenylsulfonate, 3-phenylsulfonate, or 4-phenylsulfonate. Accordingly, in some embodiments, $L^1$ may be phenyl and $L^2$ and $L^3$ may be 2-phenylsulfonate; or $L^2$ may be phenyl and $L^1$ and $L^3$ may be 2-phenylsulfonate; or $L^3$ may be phenyl and $L^1$ and $L^2$ may be 2-phenylsulfonate; or $L^1$ may be 2-phenylsulfonate and $L^2$ and $L^3$ may be phenyl; or $L^2$ may be 2-phenylsulfonate and $L^1$ and $L^3$ may be phenyl; or $L^3$ may be 2-phenylsulfonate and $L^1$ and $L^2$ may phenyl; or $L^1$ may be phenyl and $L^2$ and $L^3$ may be 3-phenylsulfonate; or $L^2$ may be phenyl and $L^1$ and $L^3$ may be 3-phenylsulfonate; or $L^3$ may be phenyl and $L^1$ and $L^2$ may be 3-phenylsulfonate; or $L^1$ may be 3-phenylsulfonate and $L^2$ and $L^3$ may be phenyl; or $L^2$ may be 3-phenylsulfonate and $L^1$ and $L^3$ may be phenyl; or $L^3$ may be 3-phenylsulfonate and $L^1$ and $L^2$ may phenyl; or $L^1$ may be phenyl and $L^2$ and $L^3$ may be 4-phenylsulfonate; or $L^2$ may be phenyl and $L^1$ and $L^3$ may be 4-phenylsulfonate; or $L^3$ may be phenyl and $L^1$ and $L^2$ may be 4-phenylsulfonate; or $L^1$ may be 4-phenylsulfonate and $L^2$ and $L^3$ may be phenyl; or $L^2$ may be 4-phenylsulfonate and $L^1$ and $L^3$ may be phenyl; or $L^3$ may be 4-phenylsulfonate and $L^1$ and $L^2$ may phenyl.

As stated above, $L^1$, $L^2$, and $L^3$ may be optionally substituted heteroaryl. An example of heteroaryl is pyridyl. The nitrogen of the pyridyl could be present at any position on the aromatic ring, relative to the phosphorus atom. For example, $L^1$ may be phenyl and $L^2$ and $L^3$ may be 2-pyridyl; or $L^2$ may be phenyl and $L^1$ and $L^3$ may be 2-pyridyl; or $L^3$ may be phenyl and $L^1$ and $L^2$ may be 2-pyridyl; or $L^1$ may be 2-pyridyl and $L^2$ and $L^3$ may be phenyl; or $L^2$ may be 2-pyridyl and $L^1$ and $L^3$ may be phenyl; or $L^3$ may be 2-pyridyl and $L^1$ and $L^2$ may phenyl; or $L^1$ may be phenyl and $L^2$ and $L^3$ may be 3-pyridyl; or $L^2$ may be phenyl and $L^1$ and $L^3$ may be 3-pyridyl; or $L^3$ may be phenyl and $L^1$ and $L^2$ may be 3-pyridyl; or $L^1$ may be 3-pyridyl and $L^2$ and $L^3$ may be phenyl; or $L^2$ may be 3-pyridyl and $L^1$ and $L^3$ may be phenyl; or $L^3$ may be 3-pyridyl and $L^1$ and $L^2$ may phenyl; or $L^1$ may be phenyl and $L^2$ and $L^3$ may be 4-pyridyl; or $L^2$ may be phenyl and $L^1$ and $L^3$ may be 4-pyridyl; or $L^3$ may be phenyl and $L^1$ and $L^2$ may be 4-pyridyl; or $L^1$ may be 4-pyridyl and $L^2$ and $L^3$ may be phenyl; or $L^2$ may be 4-pyridyl and $L^1$ and $L^3$ may be phenyl; or $L^3$ may be 4-pyridyl and $L^1$ and $L^2$ may phenyl.

In some embodiments the phosphorus atom may be substituted by $L^1$, $L^2$, and $L^3$, wherein two or more of $L^1$, $L^2$, or $L^3$ when taken together with the phosphorus atom form a heterocyclic moiety. Examples of heterocyclic moieties include and aziridinyl, azetidinyl, pyrrolidyl, piperidinyl, azepanyl, azocanyl, piperazinyl, decahydroisoquinolinyl, decahydroquinolinyl, quinuclidinyl, 1-azaadamantanyl, 2-azaadamantanyl, 1,3,5-triaza-7-phosphaadamantanyl (PTA), 3,7-diacetyl-1,3,7-triaza-5-phosphabicyclo[3.3.1] nonane (DAPTA). In a preferred embodiment, the heterocyclic moiety is a 1,3,5-triaza-7-phosphaadamantane (PTA).

It would be appreciated that in certain embodiments a hydrogen atom may be replaced with an isotope of hydrogen. For example, deuterium may be used to replace a metabolically labile hydrogen to improve the pharmacokinetics. Alternatively, tritium may be incorporated into a compound for diagnostic or analytical purposes, including but not limited to biodistribution studies.

In another aspect, the present invention provides a compound of Formula (I) which is selected from the group consisting of:

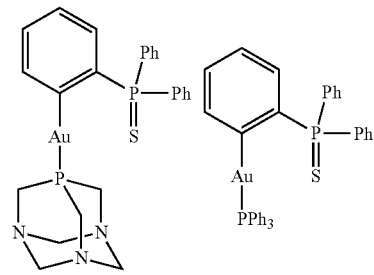

In another aspect, the present invention provides a method of treating cancer, comprising administering to a subject in need thereof a therapeutically effective amount of a compound according to Formula (I) or a pharmaceutically acceptable salt thereof.

In another aspect, the present invention provides use of a compound according to Formula (I) or a pharmaceutically acceptable salt thereof, in the preparation of a medicament for the treatment of cancer.

In another aspect, the present invention provides use of a compound according to Formula (I) or a pharmaceutically acceptable salt thereof for the treatment of cancer.

In another aspect, the present invention provides a compound according to Formula (I) or a pharmaceutically acceptable salt thereof, for use in the treatment of cancer in a subject in need thereof.

In another aspect, the present invention provides a pharmaceutical composition comprising a compound according to Formula (I) or a pharmaceutically acceptable salt thereof, and a pharmaceutically acceptable diluent, adjuvant, excipient, or carrier.

Cancer

For the present invention, cancer may be selected from the group consisting of cervical cancer, lung cancer, prostate cancer, and bone cancer. In one embodiment, the cancer is cervical cancer. In one embodiment, the cancer is lung cancer. In one embodiment, the cancer is prostate cancer. In one embodiment, the cancer is bone cancer.

Causes of Cancer

The incidence of cancer and cancer types are influenced by many factors such as age, gender, race, local environmental factors, diet, and genetics.

Anything that may cause a normal body cell to develop abnormally can potentially cause cancer. Many things can cause cell abnormalities and have been linked to cancer development. Some cancer causes remain unknown while other cancers have environmental or lifestyle triggers or may develop from more than one known cause. Some causes are influenced by a person's genetic makeup. Many patients develop cancer due to a combination of these factors. Although it is often difficult or impossible to determine the initiating event(s) that cause a cancer to develop in a specific person, research suggests a number of likely causes that alone or in concert with other causes, are the likely candidates for initiating cancer. The following is a non-exhaustive list of the major causes of cancer:

Chemical or toxic compound exposures: benzene, asbestos, nickel, cadmium, vinyl chloride, benzidine, N-nitrosamines, tobacco or cigarette smoke (contains at least 66 known potential carcinogenic chemicals and toxins), and aflatoxin;

Ionizing radiation: uranium, radon, ultraviolet rays from sunlight, radiation from alpha, beta, gamma, and X-ray-emitting sources;

Pathogens: Human papillomavirus (HPV), Epstein-Barr virus (EBV), hepatitis viruses B and C, Kaposi's sarcoma-associated herpes virus (KSHV), Merkel cell polyomavirus, *Schistosoma* spp., and *Helicobacter pylori*; other bacteria are being researched as possible agents; and Genetics: a number of specific cancers have been linked to human genes, such as breast, ovarian, colorectal, prostate, skin and melanoma.

Types of Cancer

Many cancers and the abnormal cells that compose the cancer tissue may be further identified by the name of the tissue that the abnormal cells originated from. For example, cancer types include, but are not limited to, cancer of the breast, prostate, cervix, bone, head, neck, ear, eye, mouth, nose, throat, upper jaw, tongue, lip, thyroid, esophagus, chest, lung, liver, kidney, biliary tract, ureter, bladder, stomach, upper intestine, lower intestine, colon, rectum or other gastrointestinal tract organs, spleen, skeletal muscle, subcutaneous tissue, ovaries, testicles, uterus, or other reproductive organs, skin, blood, lymph nodes, pancreas, gall bladder, brain or central nervous system.

Aside from the location that the cancer originates from, most cancers can also be classed into the following categories, according to the National Cancer Institute:

Carcinoma: cancer that begins in the skin or in tissues that line or cover internal organs;

Sarcoma: cancer that begins in bone, cartilage, fat, muscle, blood vessels, or other connective or supportive tissue;

Leukemia: cancer that starts in blood-forming tissue such as the bone marrow and causes large numbers of abnormal blood cells to be produced and enter the blood;

Lymphoma and myeloma: cancers that begin in the cells of the immune system; and

Central nervous system cancers: cancers that begin in the tissues of the brain and spinal cord.

Manifestation

Cancer can manifest in a number of different ways. For example, it can amass into a local area known as a tumour, or neoplasm, or it may be dispersed in the blood or lymphoid system, such as in various forms of leukemia.

A tumour can be malignant or benign. Malignant means the tendency of the cancer to become progressively worse. For example, a malignant tumour is capable of invading adjacent tissues, or even spreading to distant tissues. Malignant tumours are also characterized by genome instability, so that cancers, as assessed by whole genome sequencing, frequently have between 10,000 and 100,000 mutations in their entire genomes compared to healthy cells. They also frequently have reduced expression of DNA repair enzymes due to epigenetic methylation of DNA repair genes or altered microRNAs that control DNA repair gene expression.

Frequently, cancer cells can break away from the original mass of cells, travel through the blood and lymph systems, and lodge in other organs where they can again repeat the uncontrolled growth cycle. This process is termed metastatic spread or metastasis. If this occurs, the cancer is characterised by the origin of the cancer, rather than the destination. For example, if lung cancer cells spread to the breast the cancer is defined as metastatic lung cancer to breast, which is not the same as breast cancer which started in the breast.

A benign tumour lacks the ability to invade neighbouring tissue (metastasize). These characteristics are required for a tumour to be defined as cancerous and therefore benign tumours are non-cancerous. Also, benign tumours generally have a slower growth rate than malignant tumours and the tumour cells are usually more differentiated (cells have normal features). Benign tumours are typically surrounded by an outer surface (fibrous sheath of connective tissue) or remain with the epithelium. Common examples of benign tumours include moles and uterine fibroids.

Although benign tumours will not metastasize, some types may still produce negative health effects. The growth of benign tumours produces a "mass effect" that can compress tissues and may cause nerve damage, reduction of blood to an area of the body (ischaemia), tissue death (necrosis) and organ damage. The mass effect of tumours are more prominent if the tumour is within an enclosed space such as the cranium, respiratory tract, sinus or inside bones. Tumours of endocrine tissues may overproduce certain hormones, especially when the cells are well differentiated.

Although most benign tumours are not life-threatening, many types of benign tumours have the potential to become cancerous (malignant) through a process known as tumour progression. For this reason and other possible negative health effects, some benign tumours are removed by surgery. Accordingly, compounds of the invention may thus be useful in treating benign tumours before they become malignant or benign tumours which cannot be, or are not easily, removed by surgery.

In certain embodiments, the methods of treating cancer provided herein decreases the tumour size (e.g., volume or diameter) or metabolism in a subject by at least about 5%, 10%, 15%, 20%, 25%, 30%, 35%, 40%, 45%, 50%, 55%, 60%, 65%, 80%, 85%, 90%, 95%, 99%, or 100%, relative to the tumour size (e.g., volume or diameter) or metabolism rate prior to administration of the gold(I) compound. Such a reduction can be assessed by methods well known in the art, e.g., CT Scan, MRI, DCE-MRI, or PET Scan.

An administration route, formulation, and/or therapeutically effective amount of the compounds used in the present invention may be appropriately selected in response to, for example, the type of cancer, age, weight, sex, constitution, symptoms, indications and/or contraindications, or timing of treatment of a patient.

Administration

In the methods of the present invention the compounds can be administered in any form or mode which makes the compound bioavailable in the subject. One skilled in the art of preparing formulations can readily select the proper form and mode of administration depending upon the particular characteristics of the compound selected, the cancer to be treated and other relevant circumstances. We refer the reader to Remington's Pharmaceutical Sciences, 19$^{th}$ edition, Mack Publishing Co. (1995) for further information.

Administration of compounds within Formula (I) to a subject can be by any route known in the art. For example they can be administered by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose.

Examples of routes include topical administration, enteral administration (i.e. via the intestines, such as oral, gastric tube, or rectally) or parenteral administration (such as injections, e.g., intravenous, intramuscular, subcutaneous or intraperitoneal injection).

Examples of compositions suitable for topical administration include creams, lotions, eye drops, ear drops, sprays, inhalants, and the like.

Examples of compositions suitable for enteral administration include tablets, pills, granules, powders, capsules, liquid formulations, elixirs, suspensions, wafers, emulsions, syrups, suppositories, and the like.

Examples of compositions suitable for parenteral administration include injections or depot preparations such as an implantable pellet, and the like.

Compositions for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Compositions

Suitable compositions can be prepared by methods commonly employed using conventional, organic or inorganic additives, such as an excipient. Such excipients may be selected from fillers or diluents, binders, disintegrants, lubricants, flavoring agents, preservatives, stabilizers, suspending agents, dispersing agents, surfactants, antioxidants or solubilizers.

Examples of fillers or diluents include sucrose, starch, mannitol, sorbitol, lactose, glucose, cellulose, talc, calcium phosphate or calcium carbonate, and the like. Examples of binders include cellulose, carboxymethylcellulose, methylcellulose, hydroxymethylcellulose, hydroxy-propylmethylcellulose, polypropylpyrrolidone, polyvinylpyrrolidone, gelatin, gum arabic, polyethyleneglycol or starch, and the like. Examples of disintegrants include sodium starch glycolate or croscarmellose sodium, and the like. Examples of lubricants include magnesium stearate, light anhydrous silicic acid, talc or sodium lauryl sulfate, and the like. Examples of flavoring agents include citric acid or menthol, and the like. Examples of preservatives include sodium benzoate, sodium bisulfite, methylparaben or propylparaben, and the like. Examples of stabilizers include citric acid, sodium citrate or acetic acid, and the like. Examples of suspending agents include methylcellulose, polyvinyl pyrrolidone or aluminium stearate, and the like. Examples of dispersing agents include hydroxypropylmethylcellulose, and the like. Examples of surfactants include sodium lauryl sulfate, polaxamers, polysorbates, and the like. Examples of antioxidants include ethylene diamine tetraacetic acid (EDTA), butylated hydroxyl toluene (BHT), and the like. Examples of solubilizers include polyethylene glycols, SOLUTOL®, GELUCIRE®, and the like.

Preparation of Compositions

In general, the composition is prepared according to known methods in pharmaceutical chemistry. For example, tablets can be prepared by mixing the gold(I) compound, provided herein, with one or more suitable excipients, and pressing or compacting to form the powder into a solid dose.

In some embodiments, the gold(I) compound can be injected intravenously or directly into the tumour. Many pharmaceutical dosage forms are available. Preferably, pharmaceutical dosage forms suitable for injection or infusion comprise sterile aqueous solutions or dispersions. The pharmaceutical dosage form may be a sterile powder comprising the gold(I) compound, with or without one or more excipients, which is then solubilized or dispersed into a liquid carrier for injection. In all cases, the dosage form should be sterile, fluid and stable under the conditions of manufacture and storage. The liquid carrier or vehicle can be a solvent or liquid dispersion medium comprising, for example, water, ethanol, a polyol, vegetable oil, nontoxic glyceryl esters or suitable mixtures thereof.

Dosage

The amount of compound administered will preferably treat and/or reduce and/or alleviate the cancer or symptoms associated with cancer. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific cancer involved, the severity of the cancer, the response of the patient to treatment, the particular compound administered, the mode of administration, the bioavailability of the preparation administered, the dose regime selected, the use of other medications and other relevant circumstances.

A therapeutically effective amount of a compound of the present invention ranges from 0.01 mg/kg to 100 mg/kg. For example, the therapeutically effective amount may be selected from the group consisting of from 0.01 to 0.1 mg/kg, from 0.1 to 1 mg/kg, from 1 to 10 mg/kg, from 10 to 50 mg/kg, and from 50 mg to 100 mg/kg.

Compositions can be formulated to contain a daily dose, or a convenient fraction of a daily dose, in a dosage unit. The dosage may be administered as often as required to be effective. For example, the composition can be administered 3 times a day, 2 times a day, daily, every 2 days, every 3 days, every 4 days, every 5 days, every 6 days, or every 7 days, in accordance with the above dosage levels. Alternatively, the composition could be administered every other day, once per week, twice per week, biweekly, or monthly.

A medicament is a medicine or other agent used to treat an ailment or condition, such as cancer.

The medicament can be prepared, for example, by mixing the gold(I) compound with any number of excipients, solvents or other agents to form tablets, pills, granules, powders, capsules, liquid formulations, elixirs, suspensions, wafers, emulsions, syrups, injectable solutions, drops, nasal drops, sprays, inhalants, suppositories, ointments, creams, powdery liniments, liquid liniments, patches, implantable pellets, and the like.

EXAMPLES

Materials and Methods $^1$H (300 MHz), $^{19}$F (282 MHz) and $^{31}$P (121 MHz) NMR spectra were recorded on a Bruker Avance 300 spectrometer in $d_6$-DMSO or CDCl$_3$, unless otherwise stated. Chemical shifts (δ) are given in ppm and internally referenced to residual solvent signals ($^1$H), CFCl$_3$ ($^{19}$F), or external 85% H$_3$PO$_4$ ($^{31}$P). Coupling constants (J) are given in hertz.

Crystals suitable for single-crystal X-ray diffraction were obtained, where applicable, by layering a solution of the compound (in one solvent or solvents) with another solvent or solvents, or by slow evaporation from one or more solvents, as indicated below. Crystals were mounted on a glass capillary using a drop of inert oil (PARATONE) and transferred to a stream of cold nitrogen. Reflection data were collected on a Nonius Kappa CCD diffractometer equipped with a 95 mm camera and graphite monochromated Mo-Kα radiation (λ=0.71073 Å), in φ- and ω-scan modes. Data integration was carried out with DENZO software and multi-scan absorption correction was performed with the SORTAV program. Crystal structures were solved by direct methods using SIR92, SHELXS-97, or the Patterson method of SHELXS-97. Structure refinement was carried out as a full-matrix least-squares refinement on $F^2$ using SHELXL-97.

Starting Materials

Solvents were dried by standard procedures. Most syntheses were performed under dry argon with use of standard Schlenk techniques, although the solid compounds, once isolated, were air stable.

Synthesis and Characterization of Gold(I) Compounds

The preparation of exemplary compounds of the present invention is described in detail in the following Examples, but the artisan will recognize that the procedures described may be readily adapted to prepare a number of other agents of the various embodiments. For example, the preparation of non-exemplified compounds may be successfully performed by modifications apparent to those skilled in the art, e.g. by modifying the structure of starting materials, by modifying the order of addition of ingredients, by changing to other suitable ingredients known in the art, or by making routine modifications such as increasing or decreasing the temperature at various stages of the preparation.

The compounds of the present invention can be synthesised by a number of general synthetic routes, such as shown below:

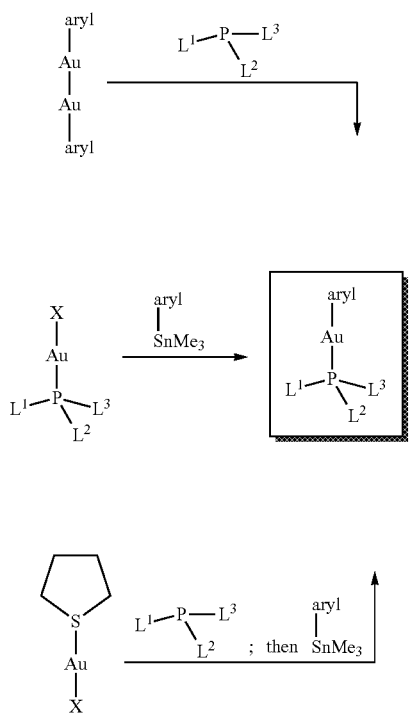

where X is a halogen atom and $L^1$, $L^2$, and $L^3$ are as defined herein. The synthesis of exemplary compounds of the present invention follows.

Example 1—Preparation of [Au(PTA){κC-2-C$_6$H$_4$P(S)Ph$_2$}] (1)

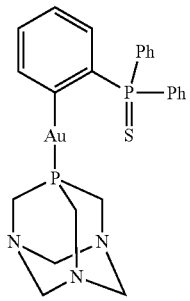

To a suspension of [Au$_2${μ-2-C$_6$H$_4$P(S)Ph$_2$}$_2$] (93 mg, 0.09 mmol) in CH$_2$Cl$_2$ (10 mL) was added PTA (30 mg, 0.19 mmol). After a few minutes, a clear colorless solution was obtained. After stirring for 15 minutes, hexane was added and the volume of the solution was reduced in vacuo, precipitating a white solid, which was isolated by filtration, washed with hexane and dried in vacuo (115 mg, 93%).

$^1$H NMR (d$_6$-DMSO): δ 3.94 (s, 6H), 4.31 (d, J=13.1 Hz, 3H), 4.45 (d, J=12.7 Hz, 3H), 6.90-7.01 (m, 2H), 7.20-7.30 (m, 1H), 7.49-7.63 (m, 7H), 7.65-7.77 (m, 4H). $^{31}$P NMR (d$_6$-DMSO): δ 44.9 (br. s), −47.8 (br. s). ESI MS (m/z): 648.1 [M+H]$^+$.

The stability in d$_6$-DMSO over 72 h was monitored by $^{31}$P NMR spectroscopy. The structure was confirmed by X-ray crystallography (crystals from CH$_2$Cl$_2$/hexane).

Example 2—Preparation of [Au(PPh$_3$){κC-2-C$_6$H$_4$P(S)Ph$_2$}] (2)

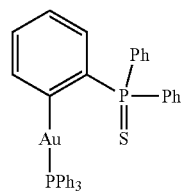

To a suspension of [Au$_2${μ-2-C$_6$H$_4$P(S)Ph$_2$}$_2$] (112 mg, 0.11 mmol) in CH$_2$Cl$_2$ (20 mL) was added PPh$_3$ (60 mg, 0.22 mmol). Almost immediately a clear, colourless solution was obtained and after stirring for 5 min, hexane was added. The volume of the solution was reduced in vacuo, precipitating a white solid, which was isolated by filtration, washed with hexane and dried in vacuo (152 mg, 88%).

$^1$H NMR (d$_6$-DMSO): δ 6.94-7.08 (m, 2H), 7.27-7.70 (m, 26H), 7.73-7.80 (m, 1H). $^{31}$P NMR (d$_6$-DMSO): δ 45.4 (d, J=8.4 Hz), 41.8 (d, J=8.4 Hz). ESI MS (m/z): 753.1 [M+H]$^+$.

The stability in d$_6$-DMSO over 72 h was monitored by $^{31}$P NMR spectroscopy. The structure was confirmed by X-ray crystallography (crystals by slow evaporation of a CH$_2$Cl$_2$ solution).

Example 3—Preparation of [Au{PPh₂(C₆H₄-3-SO₃Na)}{κC-2-C₆H₄P(S)Ph₂}] (3)

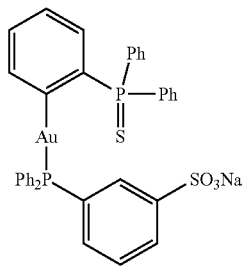

To a suspension of [Au₂{μ-2-C₆H₄P(S)Ph₂}₂] (101 mg, 0.10 mmol) in CH₂Cl₂ (25 mL) was added Ph₂PC₆H₄SO₃Na (77 mg, 0.21 mmol). The solid slowly dissolved and an almost colourless solution was obtained. After stirring for 15 min, the solution was filtered through Celite, hexane was added to the filtrate and the volume of the solution was reduced in vacuo. The white precipitated solid was isolated by filtration, washed with hexane and dried in vacuo (170 mg, 97%).

$^1$H NMR (d₆-DMSO): δ 6.98-7.09 (m, 2H), 7.28-7.71 (m, 24H), 7.77 (d, J=7.3 Hz, 2H). $^{31}$P NMR (d₆-DMSO): δ 45.4 (d, J=8.1 Hz), 42.2 (d, J=8.3 Hz). ESI MS (m/z): 833.0 [M-Na+2H]⁺, 855.0 [M+H]⁺.

The stability in d₆-DMSO over 72 h was monitored by $^{31}$P NMR spectroscopy.

Example 4—Preparation of [Au(PPh₂py){κC-2-C₆H₄P(S)Ph₂}] (4)

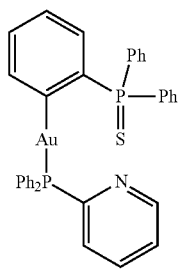

To a solution of [AuCl(tht)] (129 mg, 0.4 mmol) in CH₂Cl₂ (10 mL) was added PPh₂py (106 mg, 0.4 mmol). After stirring for 10 min, 2-Me₃SnC₆H₄P(S)Ph₂ (184 mg, 0.4 mmol) was added and stirring continued for 5 hours. The solvent was removed in vacuo to give a white solid, which was triturated with hexane then dissolved in CH₂Cl₂. After filtration through Celite, MeOH was added to the filtrate and the volume of the solution was reduced in vacuo to give a white solid. This solid was filtered off, washed with MeOH and dried in vacuo (252 mg, 83%).

$^1$H NMR (d₆-DMSO): δ 6.94-7.09 (m, 2H), 7.29-7.37 (m, 1H), 7.38-7.82 (m, 23H), 7.91 (tdd, J=1.77, 3.69, 7.70 Hz, 1H), 8.76 (dm, J=4.7 Hz, 1H). $^{31}$P NMR (d₆-DMSO): δ 45.6 (d, J=8.5 Hz), 40.9 (d, J=8.6 Hz). HR ESI MS (m/z): 754.1153. Calcd for C₃₅H₂₉NAuP₂S: 754.1161 [M+H]⁺.

The stability in d₆-DMSO over 72 h was monitored by $^{31}$P NMR spectroscopy. The structure was confirmed by X-ray crystallography (crystals from CH₂Cl₂/hexane).

Example 5—Preparation of [Au(PPh₂Fc){κC-2-C₆H₄P(S)Ph₂}] (5)

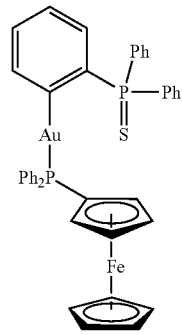

To a solution of [AuCl(PPh₂Fc)] (120 mg, 0.20 mmol) in CH₂Cl₂ (15 mL) was added Me₃SnC₆H₄P(S)Ph₂ (91 mg, 0.20 mmol) and the golden brown solution was stirred under argon overnight (ca. 22 h). The resulting yellow-orange solution was filtered through Celite, the solvent removed in vacuo and the residue triturated with hexane (2×5 mL). The solid was dissolved in CH₂Cl₂, MeOH was added and the volume reduced. The yellow precipitate was isolated by filtration, washed with MeOH and dried in vacuo (136 mg, 79%).

$^1$H NMR (CDCl₃): δ 4.13 (s, 5H), 4.29-4.32 (m, 2H), 4.43-4.47 (m, 2H), 6.94-7.14 (m, 2H), 7.28-7.55 (m, 17H), 7.74-7.83 (m, 4H), 7.93-8.00 (m, 1H). $^{31}$P NMR (CDCl₃): δ 46.3 (d, J=9.6 Hz), 36.9 (d, J=9.0 Hz). HR-ESI MS (m/z): 861.0872 [M+H]⁺.

The structure was confirmed by X-ray crystallography (crystals from CH₂Cl₂/MeOH).

Example 6—Preparation of [Au(PTA-CH₂C≡CH){κC-2-C₆H₄P(S)Ph₂}]Br (6)

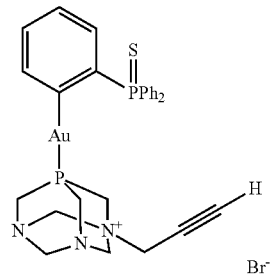

To a suspension of [Au₂{μ-2-C₆H₄P(S)Ph₂}₂] (100 mg, 0.10 mmol) in CH₂Cl₂ (20 mL) was added [PTA-CH₂C≡CH]Br (51 mg, 0.18 mmol). After stirring for 30 min, a slightly turbid solution was obtained. Addition of MeOH (1 mL) gave an almost clear solution. The volume was reduced to ca. 5 mL and filtered through Celite to remove the excess dimer starting material. Et₂O was added to the filtrate, precipitating a white solid. After stirring for 30 min, the solid was filtered off, washed with Et₂O and dried in vacuo (103 mg, 73%). Despite the use of an excess of [Au₂{μ-2-C₆H₄P(S)Ph₂}₂], the isolated product is not pure and contains a small amount of [PTA-CH₂C≡CH]Br which is in rapid equilibrium, as shown by the presence of very broad peaks in the $^{31}$P NMR spectrum.

$^{31}$P NMR (d$_6$-DMSO): δ 45.5 (br. s), 22.1 (br. s).

Example 7—Preparation of [Au(PTA-CH$_2$Ph){κC-2-C$_6$H$_4$P(S)Ph$_2$}]Br (7)

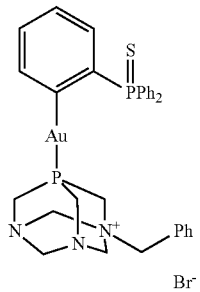

To a suspension of [Au$_2${μ-2-C$_6$H$_4$P(S)Ph$_2$}$_2$] (100 mg, 0.10 mmol) in CH$_2$Cl$_2$ (10 mL) was added [PTA-CH$_2$Ph]Br (65 mg, 0.20 mmol). After a few minutes, a MeOH was added to the clear colorless solution and the solvent was removed in vacuo. The residue was redissolved in MeOH (5 mL) and rapidly filtered through Celite. The clear solution was left to stand for 30 min, during which time a white precipitate formed. The solid was filtered off, washed with a little MeOH and dried in vacuo (125 mg, 76%).

$^1$H NMR (d$_6$-DMSO): δ 3.92 (d, J=15.0 Hz, 2H), 4.02-4.13 (m, 2H), 4.25-4.37 (m, 5H), 4.59 (d, J=13.4 Hz), 5.00 (d, J=11.3 Hz, 2H), 5.17 (d, J=11.4 Hz, 2H), 6.90-7.05 (m, 2H), 7.23-7.32 (m, 1H), 7.47-7.70 (m, 16H). $^{31}$P NMR (d$_6$-DMSO): δ 45.5 (d, J=7.3 Hz), -22.1 (d, J=9.7 Hz). ESI MS (m/z): 738.1545 [M-Br]$^+$.

The stability in d$_6$-DMSO over 72 h was monitored by $^{31}$P NMR spectroscopy. The structure has been confirmed by X-ray crystallography (crystals from MeOH).

Example 8—Preparation of [Au(DAPTA){κC-2-C$_6$H$_4$P(S)Ph$_2$}] (8)

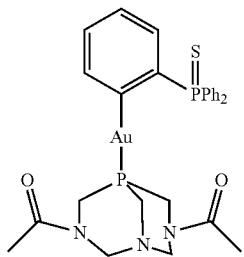

To a suspension of [Au$_2${μ-2-C$_6$H$_4$P(S)Ph$_2$}$_2$] (100 mg, 0.10 mmol) in CH$_2$Cl$_2$ (10 mL) was added DAPTA (46 mg, 0.20 mmol). After stirring for 10 min, a clear pale yellow solution was obtained. The solution was filtered through Celite and the volume of the filtrate reduced to 3 mL. Dropwise addition of Et$_2$O precipitated a white solid, which was filtered off, washed with Et$_2$O and dried in vacuo (130 mg, 89%). In d$_6$-DMSO, the $^{31}$P NMR spectrum of this compound shows the presence of 3 species (which do not change over time), but only a single species in CDCl$_3$. This suggests the DMSO solvent may coordinate to the compound forming minor amounts of two different adducts in addition to the main compound.

$^1$H NMR (CDCl$_3$): δ 2.03 (s, 3H), 2.08 (s, 3H), 3.23 (br. d, J=41.5 Hz, 1H), 3.58 (s, 2H), 3.86 (br. d, J=37.1 Hz, 1H), 4.00 (d, J=14.2 Hz, 1H), 4.18-4.33 (m, 1H), 4.56 (d, J=14.2 Hz, 1H), 4.87 (d, J=13.6 Hz, 1H), 5.22 (br. d, J=41.5 Hz, 1H), 5.71 (d, J=14.4 Hz, 1H), 6.87-7.01 (m, 2H), 7.29-7.37 (m, 1H), 7.40-7.56 (m, 6H), 7.67-7.78 (m, 4H), 7.80-7.88 (m, 1H). $^{31}$P NMR (CDCl$_3$): δ 46.4 (d, J=4.8 Hz), -19.7 (s).
$^1$H NMR (d$_6$-DMSO): δ 1.94 (br. s, 5H), 2.01 (br. s, 1H), 3.33-3.44 (m, 1.2H), 3.54-3.78 (m, 2.1H), 3.84-4.01 (m, 0.9H), 4.06 (d, J=13.2 Hz, 0.8H), 4.30 (dd, J=8.6, 15.5 Hz, 0.8H), 4.52-4.66 (m, 1.2H), 4.70-4.81 (m, 0.2H), 4.87 (d, J=14.0 Hz, 0.8H), 5.00-5.07 (m, 1H), 5.24-5.33 (m, 0.2H), 5.47 (d, J=14.1 Hz, 0.8H), 6.90-7.05 (m, 2H), 7.24-7.33 (m, 1H), 7.50-7.63 (m, 7H), 7.67-7.74 (m, 4H). $^{31}$P NMR (d$_6$-DMSO): δ 45.1 (d, J=8.5 Hz), -18.4 (d, J=8.6 Hz), together with two small intensity peaks at δ-15.3 (d, J=9.4 Hz) and -19.7 (d, J=8.4 Hz). HR-ESI MS (m/z): 720.1275 [M+H]$^+$.

The stability in d$_6$-DMSO over 72 h was monitored by $^{31}$P NMR spectroscopy. The structure has been confirmed by X-ray crystallography (crystals from acetone/hexane).

Example 9—Preparation of [Au(PTA-CH$_3$){κC-2-C$_6$H$_4$P(S)Ph$_2$}]PF$_6$ (9)

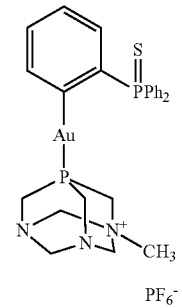

To a suspension of [Au$_2${μ-2-C$_6$H$_4$P(S)Ph$_2$}$_2$] (100 mg, 0.10 mmol) in CH$_2$Cl$_2$ (20 mL) was added [PTA-CH$_3$]PF$_6$ (64 mg, 0.20 mmol). After 5 mins, a slightly turbid solution was obtained, which then precipitated a white solid. After stirring the mixture of 60 min, the solid was filtered off and dissolved in acetone. After filtration through Celite, the volume was reduced and Et$_2$O added. A sticky yellow solid formed together with a white suspension. The suspension was carefully decanted from the solid. The solid was redissolved in acetone, Et$_2$O added and again, a sticky yellow solid and white suspension was obtained. The suspension was decanted from the solid. This acetone/Et$_2$O process was repeated two more times. Finally, the combined white suspensions were reduced in volume and Et$_2$O added, precipitating out a white solid. This was filtered off, washed with Et$_2$O and dried in vacuo (110 mg, 65%).

$^1$H NMR (d$_6$-DMSO): δ 2.73 (s, 3H), 3.88 (d, J=15.2 Hz, 2H), 4.13 (d, J=15.6 Hz, 2H), 4.25 (d, J=13.2 Hz, 1H), 4.49 (s, 2H), 4.56 (d, J=13.3 Hz, 1H), 4.86 (d, J=11.5 Hz, 2H), 5.05 (d, J=11.6 Hz, 2H), 6.91-7.07 (m, 2H), 7.25-7.34 (m, 1H), 7.50-7.74 (m, 11H). $^{31}$P NMR (d$_6$-DMSO): δ 45.5 (br. s), -25.5 (br. s), -144.2 (sept, J=711 Hz). HR-ESI MS (m/z): 662.1206 [M-PF$_6$]$^+$.

The stability in d₆-DMSO over 72 h was monitored by ³¹P NMR spectroscopy. The structure has been confirmed by X-ray crystallography (crystals from acetone/hexane).

Example 10 Preparation of [Au(PTA){κC—C₆H₃-5-F-2-P(S)Ph₂}]

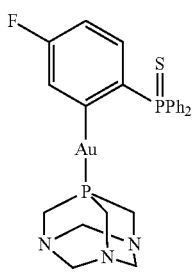

Step (1) Preparation of 2-Me₃Sn-4-F—C₆H₃P(S)Ph₂

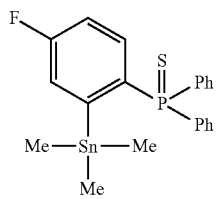 [SMILES: [CH3][Sn]([CH3])([CH3])[c]1cc(F)ccc1P(=S)(c1ccccc1)c1ccccc1]

To a solution of 2-Me₃Sn-4-F—C₆H₃PPh₂ (3.53 g, 7.97 mmol) in CH₂Cl₂ (40 mL) was added sulfur powder (270 mg, 8.42 mmol) and the mixture was stirred overnight. The solvent was removed in vacuo and the residue was recrystallised from hot ethanol (hot filtration) to give colorless crystals (2.82 g, 75%). The mother liquor was concentrated yielding an addition crop of colorless crystals (0.45 g, combined yield 87%).

¹H NMR (CDCl₃): δ 0.17 (s with unresolved ¹¹⁷/¹¹⁹Sn satellites, $J_{SnH}$=54.6 Hz, 9H), 6.87 (tt, J=2.1, 8.3 Hz, 1H), 7.00 (ddd, J=5.4, 8.4, 12.4 Hz, 1H), 7.40-7.67 (m, 11H). ¹³C NMR (CDCl₃): δ−3.76 (s with ¹¹⁷/¹¹⁹Sn satellites, $J_{SnC}$=359, 375 Hz), 113.9 (dd, J=14.2, 21.0 Hz), 125.6, (dd, J=18.4, 19.7 Hz), 128.5 (d, J=12.4 Hz), 131.6 (d, J=3.0 Hz), 132.4 (d, J=10.6 Hz), 133.4 (d, J=83.9 Hz), 134.5 (dd, J=3.2, 95.4 Hz), 134.8 (dd, J=7.4, 17.7 Hz), 154.2 (dd, J=3.3, 25.7 Hz), 163.6 (dd, J=3.4, 257 Hz). ¹⁹F NMR (CDCl₃): δ−109.8 (d, J=4.5 Hz). ³¹P NMR (CDCl₃): δ 46.9 (d, J=4.5 Hz, with unresolved ¹¹⁷/¹¹⁹Sn satellites, $J_{SnP}$=41.1 Hz).

Step (2) Preparation of [Au₂{μ-C₆H₃-5-F-2-P(S)Ph₂}₂]

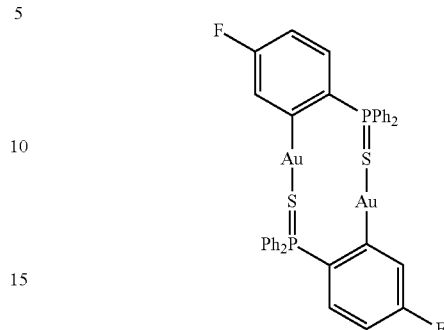

To a solution of 2-Me₃Sn-4-F—C₆H₃P(S)Ph₂ (445 mg, 0.94 mmol) in CH₂Cl₂ (10 mL) was added a solution of [AuCl(tht)] (300 mg, 0.94 mmol) in CH₂Cl₂ (10 mL) and the mixture was stirred for 30 min. Hexane was added to the mixture and the volume of the solution was reduced in vacuo. The pale yellow solid that precipitated was isolated by filtration, washed with hexane and dried in vacuo (440 mg, 93%).

¹H NMR (CDCl₃): δ 6.58 (tt, J=3.1, 8.6 Hz, 2H), 6.84 (ddd, J=5.4, 8.5, 11.9 Hz, 2H), 7.46-7.55 (m, 10H), 7.58-7.66 (m, 4H), 7.69-7.76 (m, 8H). ¹⁹F NMR (CDCl₃): δ 109.3 (d, J=5.2 Hz). ³¹P NMR (CDCl₃): δ 48.6 (d, J=5.1 Hz).

Step 3 Preparation of [Au(PTA){κC—C₆H₃-5-F-2-P(S)Ph₂}]

To a solution of [Au₂{μ-C₆H₃-5-F-2-P(S)Ph₂}₂] (100 mg, 0.1 mmol) in CH₂Cl₂ (5 mL) was added PTA (31 mg, 0.2 mmol). After a few minutes, a clear colorless solution was obtained. After stirring for 15 minutes, hexane was added and the volume of the solution was reduced in vacuo, precipitating a white solid. The solid was isolated by filtration, washed with hexane and dried in vacuo (125 mg, 95%).

¹H NMR (d₆-DMSO): δ 3.95 (s, 6H), 4.31 (d, J=13.2 Hz, 3H), 4.45 (d, J=12.8 Hz, 3H), 6.70-6.84 (m, 1H), 6.95-7.07 (m, 1H), 7.27-7.37 (m, 1H), 7.50-7.63 (m, 6H), 7.64-7.76 (m, 4H). ¹⁹F NMR (d₆-DMSO): δ−111.9 (dd, J=4.8, 5.1 Hz). ³¹P NMR (d₆-DMSO): δ 44.7 (dd, J=5.9, 7.2 Hz), −48.7 (dd, J=5.1, 7.2 Hz).

The stability in d₆-DMSO over 72 h was monitored by ³¹P NMR spectroscopy. The structure was confirmed by X-ray crystallography (crystals from CH₂Cl₂/hexane).

Example 11 Preparation of [Au(PTA){κC—C₆H₃-5-Me-2-P(S)Ph₂}]

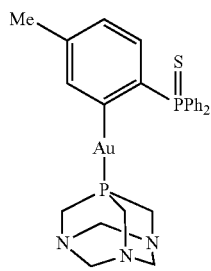

Step 1 Preparation of 2-Me₃Sn-4-Me-C₆H₃P(S)Ph₂

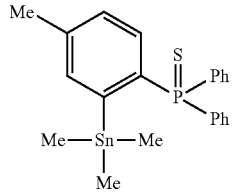 [SMILES: Cc1ccc(P(=S)(c2ccccc2)c2ccccc2)[c]([Sn]([CH3])([CH3])[CH3])c1]

To a solution of 2-Me₃Sn-4-Me-C₆H₃PPh₂ (4.00 g, 9.11 mmol) in CH₂Cl₂ (40 mL) was added sulfur powder (300 mg, 9.36 mmol) and the mixture wad stirred overnight. The solvent was removed in vacuo and the residue was recrystallised from hot ethanol (hot filtration) to give colorless crystals (3.93 g, 92%).

¹H NMR (CDCl₃): δ 0.16 (s with unresolved $^{117/119}$Sn satellites, $J_{SnH}$=54.1 Hz, 9H), 2.39 (s, 3H), 6.91 (dd, J=7.9, 12.7 Hz, with unresolved $^{117/119}$Sn satellites, $J_{SnH}$=15.6 Hz, 1H), 6.98-7.07 (m, 1H), 7.36-7.55 (m, 6H), 7.56-7.79 (m, 5H). ¹³C NMR (CDCl₃): δ −3.93 (s with $^{117/119}$Sn satellites, $J_{SnC}$=354, 370 Hz), 21.4 (d, J=1.9 Hz), 127.9 (d, J=12.9 Hz, with unresolved $^{117/119}$Sn satellites, $J_{SnC}$=9.9 Hz), 128.4, (d, J=12.3 Hz), 131.3 (d, J=2.9 Hz), 132.4 (d, J=10.5 Hz), 132.8 (d, J=15.8 Hz), 133.7 (d, J=83.3 Hz), 135.6 (d, J=94.5 Hz, with unresolved $^{117/119}$Sn satellites, $J_{SnC}$=28.5 Hz), 139.6 (d, J=18.5 Hz, with unresolved $^{117/119}$Sn satellites, $J_{SnC}$=33.9 Hz), 140.2 (d, J=3.3 Hz, with unresolved $^{117/119}$Sn satellites, $J_{SnC}$=42.3 Hz), 149.4 (d, J=23.5 Hz, with $^{117/119}$Sn satellites, $J_{SnC}$=436, 457 Hz). ³¹P NMR (CDCl₃): δ 47.6 (s with unresolved $^{117/119}$Sn satellites, $J_{SnP}$=47.6 Hz).

Step 2—Preparation of [Au₂{μ-C₆H₃-5-Me-2-P(S)Ph₂}₂]

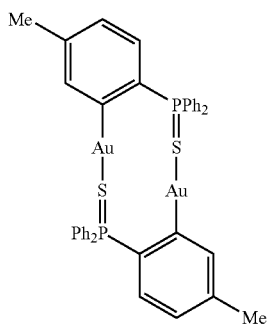

To a solution of 2-Me₃Sn-4-Me-C₆H₃P(S)Ph₂ (600 mg, 1.27 mmol) in CH₂Cl₂ (10 mL) was added a solution of [AuCl(tht)] (408 mg, 1.27 mmol) in CH₂Cl₂ (10 mL). The colorless solution turned orange and was stirred for 30 min. Hexane was added to the mixture and the volume of the solution was reduced in vacuo. The pale yellow solid that precipitated was isolated by filtration, washed with hexane and dried in vacuo (560 mg, 87%).

¹H NMR (CDCl₃): δ 2.23 (s, 6H), 6.67-6.78 (m, 4H), 7.45-7.54 (m, 8H), 7.55-7.63 (m, 4H), 7.65-7.76 (m, 10H). ³¹P NMR (CDCl₃): δ 48.1 (s).

Step 3 Preparation of [Au(PTA){κC—C₆H₃-5-Me-2-P(S)Ph₂}]

To a solution of [Au₂{μ-C₆H₃-5-Me-2-P(S)Ph₂}₂] (103 mg, 0.1 mmol) in CH₂Cl₂ (5 mL) was added PTA (32 mg, 0.2 mmol) and the mixture stirred for 15 minutes. Hexane was added to the pale yellow solution and the volume was reduced in vacuo, precipitating a white solid. The solid was isolated by filtration, washed with hexane and dried in vacuo (129 mg, 96%).

¹H NMR (d₆-DMSO): δ 2.21 (s, 3H), 3.94 (s, 6H), 4.30 (d, J=13.0 Hz, 3H), 4.45 (d, J=12.7 Hz, 3H), 6.74-6.83 (m, 1H), 6.90 (dd, J=8.0, 11.9 Hz, 1H), 7.37 (br. d, J=4.5 Hz, 1H), 7.49-7.61 (m, 6H), 7.64-7.75 (m, 4H). ³¹P NMR (d₆-DMSO): δ 44.7 (d, J=8.7 Hz), −47.5 (d, J=8.7 Hz). The stability in d₆-DMSO over 72 h was monitored by ³¹P NMR spectroscopy.

Example 12 Preparation of [Au(PTA){κC—C₆H₃-6-Me-2-P(S)Ph₂}]

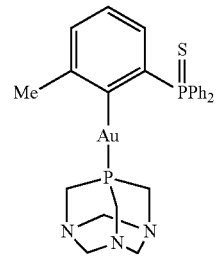

Step 1—Preparation of 2-Me₃Sn-3-Me-C₆H₃P(S)Ph₂

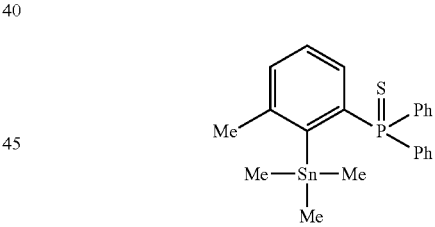

To a solution of 2-Me₃Sn-3-Me-C₆H₃PPh₂ (4.00 g, 9.11 mmol) in CH₂Cl₂ (25 mL) was added sulfur powder (300 mg, 9.36 mmol) and the mixture was stirred overnight. The solvent was removed in vacuo and the residue was recrystallised from hot ethanol (hot filtration) to give colorless crystals (3.48 g, 81%).

¹H NMR (CDCl₃): δ 0.17 (s with $^{117/119}$Sn satellites, $J_{SnH}$=53.0, 54.6 Hz, 9H), 2.57 (s, 3H), 6.78 (dd, J=7.3, 13.9 Hz, 1H), 7.05 (dt, J=3.4, 7.6 Hz, 1H), 7.20-7.30 (m, 1H), 7.39-7.56 (m, 6H), 7.62-7.73 (m, 4H). ¹³C NMR (CDCl₃): δ −1.05 (s with $^{117/119}$Sn satellites, $J_{SnC}$=347, 363 Hz), 25.9 (s with unresolved $^{117/119}$Sn satellites, $J_{SnC}$=30.6 Hz), 127.0 (d, J=13.7 Hz), 128.4, (d, J=12.4 Hz), 130.8 (d, J=15.7 Hz), 131.4 (d, J=3.0 Hz), 132.4 (d, J=3.4 Hz), 132.6 (d, J=10.5 Hz), 133.8 (d, J=83.0 Hz), 140.1 (d, J=91.5 Hz), 147.0 (d, J=17.9 Hz), 149.9 (d, J=22.7 Hz). ³¹P NMR (CDCl₃): δ 49.0 (s with unresolved $^{117/119}$Sn satellites, $J_{SnP}$=56.2 Hz).

Step 2—Preparation of [Au$_2${µ-C$_6$H$_3$-6-Me-2-P(S)Ph$_2$}$_2$]

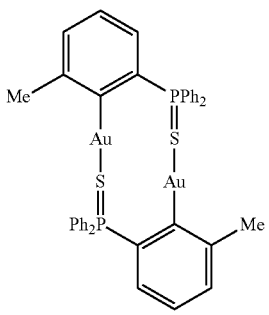

To a solution of 2-Me$_3$Sn-3-Me-C$_6$H$_3$P(S)Ph$_2$ (600 mg, 1.27 mmol) in CH$_2$Cl$_2$ (10 mL) was added a solution of [AuCl(tht)] (408 mg, 1.27 mmol) in CH$_2$Cl$_2$ (10 mL). The colorless solution turned bright yellow and was stirred for 30 min, during which time became slightly turbid. Hexane was added to the mixture and the volume of the solution was reduced in vacuo. The yellow solid that precipitated was isolated by filtration, washed with hexane and dried in vacuo (635 mg, 99%).

$^1$H NMR (CDCl$_3$): δ 2.36 (s, 6H), 6.65 (dd, J=7.6, 12.7 Hz, 2H), 6.83 (dt, J=5.2, 7.6 Hz, 2H), 7.17 (dd, J=1.7, 7.5 Hz, 2H), 7.44-7.54 (m, 8H), 7.54-7.62 (m, 4H), 7.74-7.84 (m, 8H). $^{31}$P NMR (CDCl$_3$): δ 48.7 (s).

Step 3—Preparation of [Au(PTA){κC—C$_6$H$_3$-6-Me-2-P(S)Ph$_2$}]

To a suspension of [Au$_2${µ-C$_6$H$_3$-6-Me-2-P(S)Ph$_2$}$_2$] (103 mg, 0.1 mmol) in CH$_2$Cl$_2$ (5 mL) was added PTA (32 mg, 0.2 mmol). Almost immediately a pale yellow solution was obtained, which was stirred for 10 min. Hexane was added to the solution and the volume was reduced in vacuo. The precipitated white solid was isolated by filtration, washed with hexane and dried in vacuo (124 mg, 92%).

$^1$H NMR (d$_6$-DMSO): δ 2.45 (s, 3H), 3.95 (s, 6H), 4.31 (d, J=13.0 Hz, 3H), 4.46 (d, J=12.7 Hz, 3H), 6.73 (dd, J=7.6, 12.1 Hz, 1H), 6.90 (dt, J=4.6, 7.5 Hz, 1H), 7.20 (br. d, J=7.2 Hz, 1H), 7.49-7.61 (m, 6H), 7.63-7.75 (m, 4H). $^{31}$P NMR (d$_6$-DMSO): δ 44.5 (d, J=8.5 Hz), −46.5 (d, J=8.5 Hz). The stability in d$_6$-DMSO over 72 h was monitored by $^{31}$P NMR spectroscopy.

Example 13—In Vitro Testing

Cell Culture

Prostate (PC-3), cervical (HeLa), lung (A549), fibrosarcoma (bone, HT1080), and human embryonic kidney (Hek-293) cells were purchased from ATCC. PC-3 and HeLa cells were grown in RPMI medium, whereas HT1080 and Hek-293 were maintained in DMEM medium supplemented with 10% FBS and 1% PS. All cells were maintained in a sterile incubator with 75% humidity and 5% CO$_2$ at 37° C. Cells were harvested with 0.25% trypsin-ethylenediaminetetraacetic acid (EDTA, Life Technologies) for subculture and plating after reaching 80% confluence. For all the assays, unless otherwise mentioned, stock solutions of the metal compounds were freshly prepared in DMSO (10 mM) and 1% DMSO in complete medium was used as a control. Cisplatin (positive control) was purchased from Sigma-Aldrich.

MTT Assay (In Vitro Cytotoxicity)

The MTT [3-(4,5-dimethylthiazol-2-yl)-2,5-diphenyltetrazolium bromide] assay is based on the conversion of a yellow coloured MTT solution to purple formazan crystals by the active mitochondrial dehydrogenases of viable cells. Thus, the intensity of the produced purple colour is proportional to the number of viable cells. The cells were seeded in 96 well plates depending on cellular doubling time and were treated with solutions of the metal compounds (100 µM, 10 µm, 1 µM, 0.1 µM, 0.01 µM) after overnight incubation. The cells were further incubated for 48 h and the medium containing the test compounds was removed before addition of 100 µL MTT solution (5 mg/mL) in serum-free medium. After 4 h incubation in the dark at 37° C., the excess MTT solution was removed from the wells and 100 µL of DMSO was added to each well to solubilise the formed formazan crystals. The absorbance of formazan solution from each well was recorded using a Spectramax micro titre plate reader at 570 and 630 nm. Growth inhibition of the compounds was calculated as IC50 values (concentration of compound that causes 50% inhibition of cell growth) using Probit software. Each experiment was repeated three times and the standard deviation values are reported in Table 1. All cells were maintained in an incubator humidified atmosphere containing 95% air and 5% CO$_2$ at 37° C. Cells were harvested with 0.25% trypsin-EDTA (Life Technologies) for subculture and plating for drug treatments when they reached 80% confluence. For all the assays, stock solutions of gold compounds were prepared in DMSO (10 mM) and the final treatment concentrations (100 µM-0.01 µM) were made in complete growth medium. Results are also summarised in FIG. 8.

The results of the in vitro testing are summarised in Table 1, below:

TABLE 1

In vitro cytotoxicity (IC$_{50}$ values in µM) of gold(I) compounds on different cancer cell lines

| Compound | HeLa (cervical) | A549 (lung) | PC3 (prostate) | HT-1080 (bone) | HeK-293 (normal) |
|---|---|---|---|---|---|
| 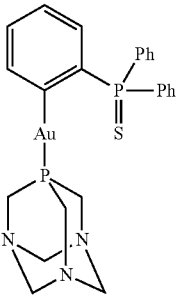 | 0.12 ± 0.02 | 3.46 ± 0.13 | 1.81 ± 0.26 | 0.08 ± 0.01 | 0.38 ± 0.11 |

TABLE 1-continued

In vitro cytotoxicity (IC$_{50}$ values in μM) of gold(I) compounds on different cancer cell lines

| Compound | HeLa (cervical) | A549 (lung) | PC3 (prostate) | HT-1080 (bone) | HeK-293 (normal) |
|---|---|---|---|---|---|
| 2 | 10.51 ± 1.5 | 4.57 ± 0.61 | 3.73 ± 0.43 | 0.57 ± 0.1 | 5.81 ± 0.35 |
| 3 | 9.13 ± 0.82 | >50 | 5.22 ± 0.22 | 3.09 ± 0.16 | 6.31 ± 0.66 |
| 4 | 1.35 ± 0.23 | >50 | 0.61 ± 0.08 | 6.65 ± 0.35 | 0.95 ± 0.2 |
| Cisplatin | 3.25 ± 0.11 | 5.69 ± 0.37 | 6.31 ± 0.52 | 0.63 ± 0.06 | 4.78 ± 0.33 |

$^a$IC$_{50}$ values are the concentrations that cause 50% inhibition of cancer cell growth (μM).
Data represent the mean values ± standard deviation of three independent expeeriments performed in triplicate.
HeLa—cervical cancer;
A549—lung cancer;
PC-3—prostate cancer;
HT-1080—bone cancer;
Hek-293—Human embryonic kidney cells.

The newly synthesised gold compounds displayed excellent in vitro anti-cancer activities in preliminary studies and showed more potent and broad spectrum cytotoxicity on different cancer cell lines as compared to cisplatin. In particular, gold compound 1 showed approximately 27-fold higher cytotoxicity than cisplatin towards cervical cancer cells and 3.5- and 7.8-fold higher cytotoxicity against prostate and bone cancer cells respectively. The gold compound 1 also showed 3 and 4-fold selectivity towards cervical and bone cancer cells compared to the non-cancerous HeK-293 cells.

Figure 8:
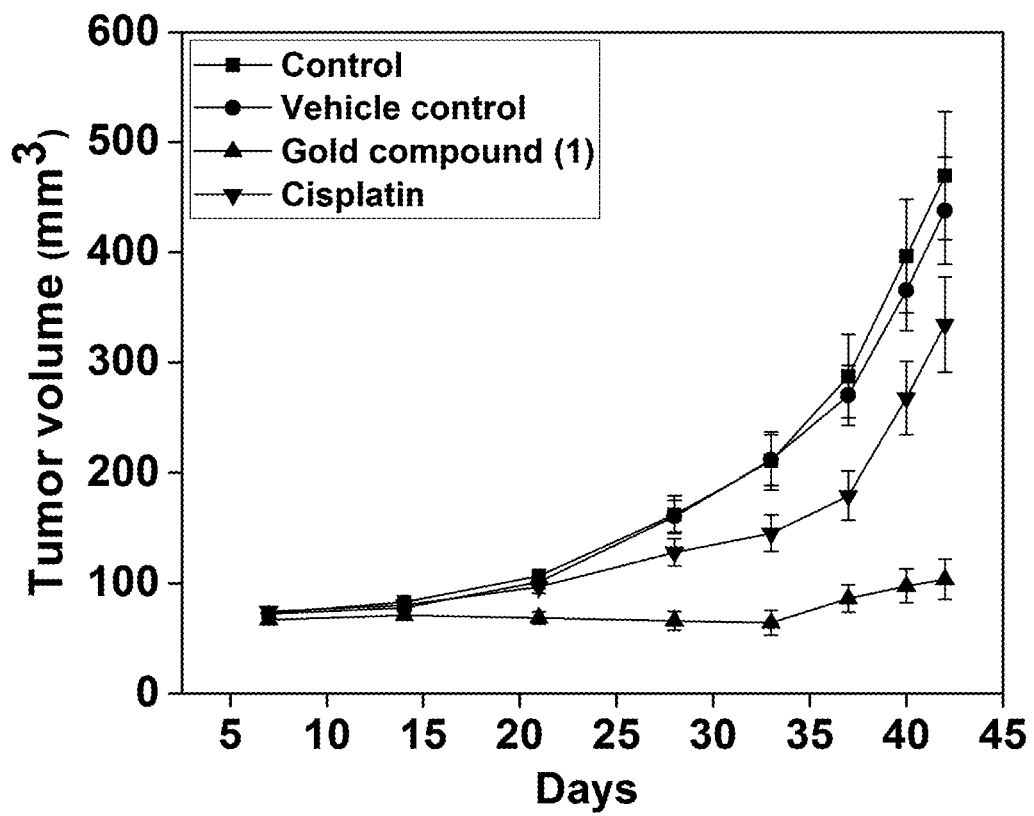
FIG. 8. Anti-tumour activity of gold compound 1 in mice bearing HeLa xenografts. Graph shows tumour volume (mm$^3$) after intraperitoneal administration of control or metal compounds (1 mg/kg).

The results from FIG. 8 show that significant tumour volume inhibition (81%) was observed for the gold compound treatment compared to those treated with solvent control.

Example 14—In Vivo Anti-Tumour Activity in Mice Xenograft Models

The use of metal complexes or gold compounds in animal xenograft models has been previously described elsewhere for cervical cancer models or other tumour types. The efficacy of the newly synthesised novel gold compound in reducing tumour growth in cervical cancer models was tested as follows. The most potent gold compound was tested in mice xenograft models against cervical cancer cell line (HeLa). Five-week-old female BALB/c Nude mice were used. HeLa tumour cells (5×10$^6$) resuspended in RPMI medium injected subcutaneously tumour cells in 100 μL of culture media using a 29-gauge insulin syringe into both ventral flanks, anterior to the hind leg. The mice were monitored twice daily for 48 hrs to determine if any unexpected adverse effects are observed. Tumours were allowed to establish to approximately 50 mm³ (as determined using electronic callipers) and the mice were then randomly separated into three groups of 5. Then mice were injected with intraperitoneal doses of either the vehicle control, 1 mg/kg of the gold compound 1, or cisplatin every three days for 42 days (a total of 13 injections per animal).

For preparing drug solutions, gold compound 1 and cisplatin were separately dissolved DMSO to give a final concentration of 2.5 mg/mL. From this stock solution, the final working concentrations for mice injections were prepared in PBS (Phosphate buffered saline, pH 7.4) with DMSO concentration not exceeding 3.6%. Then mice were injected with 200 μL intraperitoneal doses of either the vehicle control (3.6% DMSO in PBS), 1 mg/kg of the gold compound 1 or cisplatin three days a week for 42 days (a total of 19 injections per animal).

Figure 10:
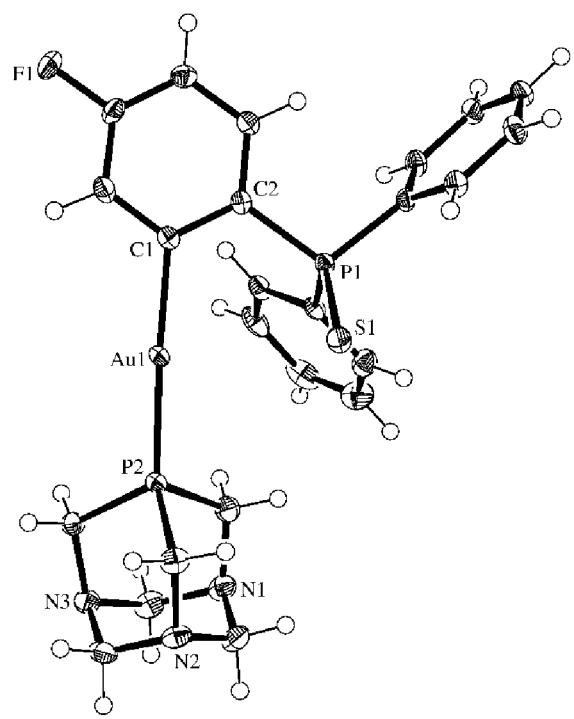
FIG. 10. Molecular structure of [Au(PTA){κC—$C_6H_3$-5-F-2-P(S)$Ph_2$}]: (Example 10). Ellipsoids show 50% probability levels. Hydrogen atoms have been omitted for clarity.
Figure 11:
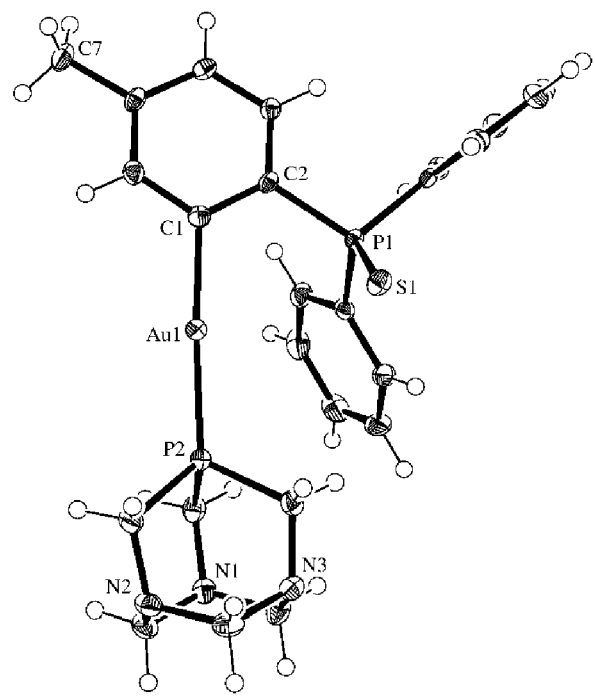
FIG. 11. Molecular structure of [Au(PTA){κC—$C_6H_3$-5-Me-2-P(S)$Ph_2$}]: (Example 11). Ellipsoids show 50% probability levels. Hydrogen atoms have been omitted for clarity.
Figure 12:
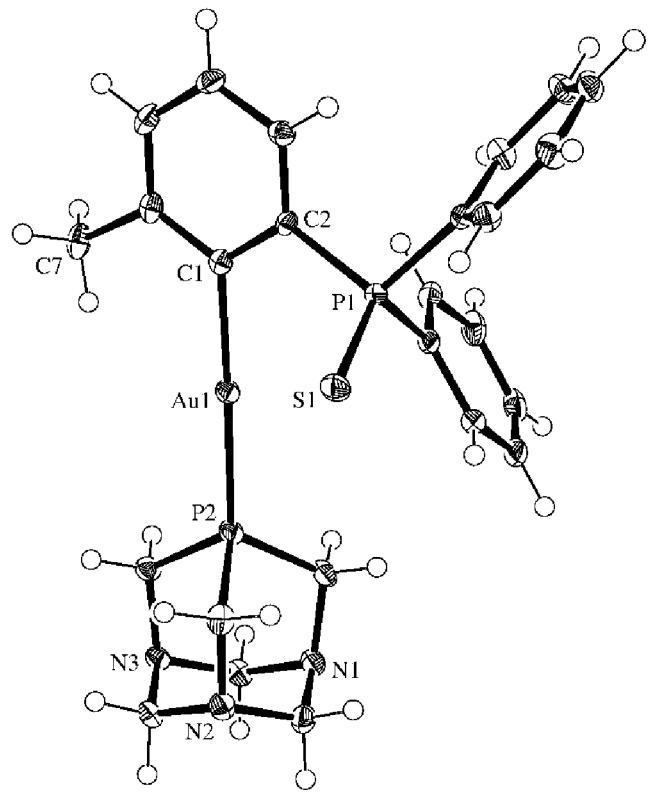
FIG. 12. Molecular structure of [Au(PTA){κC—$C_6H_3$-6-Me-2-P(S)$Ph_2$}]: (Example 12). Ellipsoids show 50% probability levels. Hydrogen atoms have been omitted for clarity.

Tumour volumes were measured 8 times during the 42-day period. All mice were culled after 42 days and the tumours were collected and weighed. All the animal experiments were performed in Biological Research Facility, Melbourne University according to the animal ethics number 1814422. Representative results are shown in FIG. 10.

The in vivo anti-tumour activity was examined in nude mice bearing HeLa xenografts with 1 mg/kg of the most active compound 1 and cisplatin through intraperitoneal (i.p.) injection once every three days.

Figure 9:
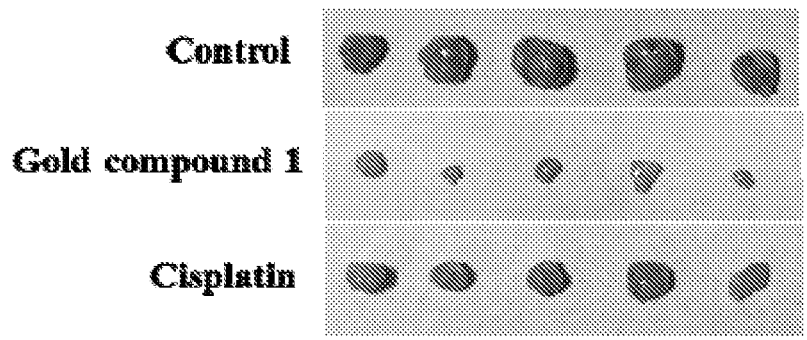
FIG. 9. Representative images of tumours after 42 days of treatment.

Results in FIG. 9 depict representative tumours after 42 days of treatment, clearly showing superior performance of compound 1 compared to cisplatin. In addition, no mouse death or body weight loss was observed after the treatment with the gold compound at this dose. In contrast, treatment with cisplatin resulted in 29% of the tumour volume inhibition.

Example 15—Testing of Compound 1 Versus Cisplatin in a Dose Dependent Study

A dose dependent study of compound 1, cisplatin and etoposide was conducted using the trypan blue assay to determine the dose dependent toxicity towards cisplatin-resistant ovarian cancer cells (A2780Cis). The results are shown in FIG. 13.

Figure 13:
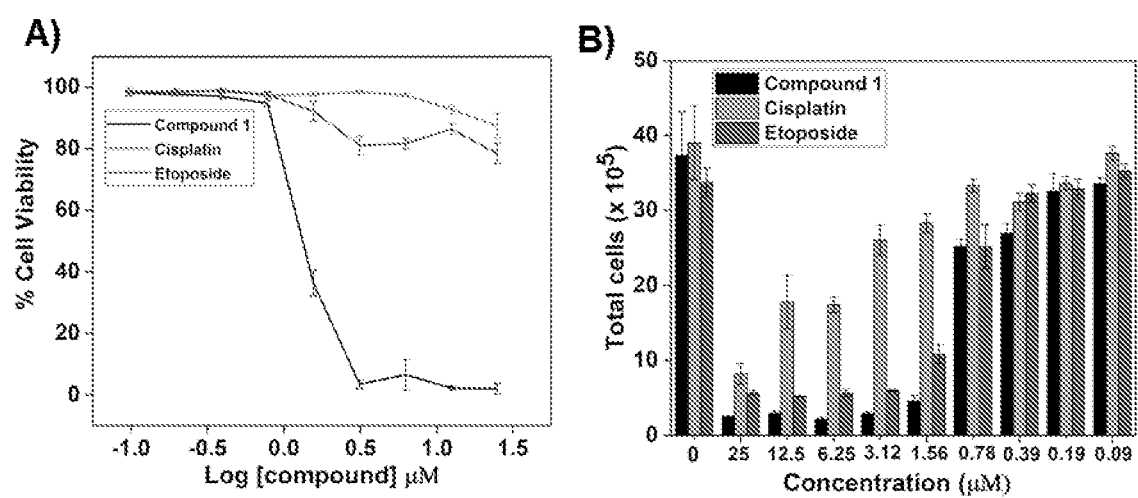
FIG. 13. The effect of compound 1, cisplatin and etoposide on (A) viability and (B) total cell count after 72 hours treatment of cisplatin-resistant ovarian cancer cells (A2780Cis).

Compound 1 showed a dose-dependent increase in cytotoxicity towards A2780Cis cells, even at lower concentrations (80% cell death at 0.39 μM), whereas the clinically-used drugs cisplatin and etoposide showed no significant effect on cell viability at the same concentration (FIG. 13).

Example 16—In Vitro Testing—Trypan Blue Assay

A Trypan blue assay was conducted to determine the cytotoxicity of certain compounds of the invention towards cisplatin-sensitive (A2780) and -resistant (A2780Cis) ovarian, prostate (PC3) and colon (HT-29) cancer cells.

In order to determine the toxicity of the compounds, 5×10⁴ cells per well were seeded into 24 well plates and allowed to grow for 24 hours. The cells were then treated with increasing concentrations of the compounds for 72 hours. Cisplatin was dissolved in PBS at 1 mM concentration. The gold complexes were dissolved in DMSO immediately prior to the experiments (5 mM stock solutions). 0.25% DMSO in complete medium served as vehicle control. All treatments were performed using molar concentrations and each well received 1 mL of treatment in cell culture media (RPMI) containing 10% FBS and 1% penicillin and streptomycin. After 72 hours of treatment, the media was collected from each well in separate tubes in order to include dead cells in the cell count. Cells from the plate were removed using 200 μL of 0.25% Trypsin-EDTA for 3 minutes at 37° C. Trypsin was neutralised with the media originally removed from the cells and centrifuged at 1200 rpm for 5 minutes. The supernatant was discarded and the cells were resuspended in 100 μL of fresh complete media. From this, 20 μL of cell suspension was removed, mixed with an equal volume of Trypan Blue and the cells were counted using a haemocytometer. The results are shown in Table 2.

TABLE 2

In vitro cytotoxicity (IC$_{50}$ - μM) of certain complexes of the invention and cisplatin.

| Test Compound | A2780Cis | A2780 | PC3 | HT-29 |
|---|---|---|---|---|
| 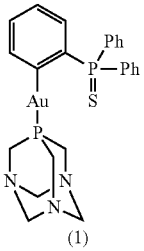 (1) | 1.45 ± 0.12 | 0.11 ± 0.02 | 1.81 ± 0.26 | 1.79 ± 0.12 |
| 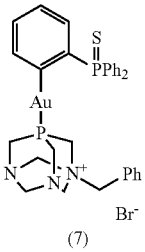 (7) | 0.27 ± 0.01 | 0.25 ± 0.03 | 0.39 ± 0.08 | 3.74 ± 0.29 |
| 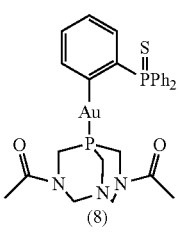 (8) | 0.42 ± 0.12 | 0.30 ± 0.02 | 0.14 ± 0.03 | 6.32 ± 0.36 |
| 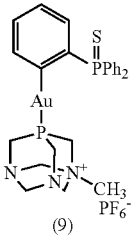 (9) | 1.41 ± 0.09 | 0.48 ± 0.05 | 0.47 ± 0.11 | 10.1 ± 0.96 |
| 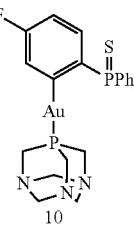 10 | 0.50 ± 0.07 | 0.12 ± 0.05 | 0.42 ± 0.02 | 1.83 ± 0.13 |

TABLE 2-continued

In vitro cytotoxicity (IC$_{50}$ - μM) of certain complexes of the invention and cisplatin.

| Test Compound | A2780Cis | A2780 | PC3 | HT-29 |
|---|---|---|---|---|
| 11 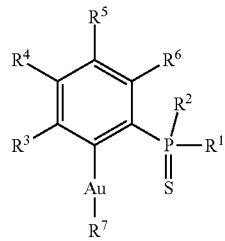 | 0.42 ± 0.09 | 0.35 ± 0.13 | 0.50 ± 0.06 | 3.26 ± 0.24 |
| 12 | 0.65 ± 0.05 | 0.26 ± 0.06 | 0.56 ± 0.08 | 2.30 ± 0.14 |
| auranofin | 0.71 ± 0.06 | 0.08 ± 0.01 | 0.44 ± 0.05 | 0.51 ± 0.04 |
| cisplatin | >25 | 1.40 ± 0.13 | 6.31 ± 0.52 | >25 |

A2780Cis—Cisplatin resistant ovarian cancer cells;
A2780—Ovarian cancer cells;
PC3—Prostate cancer cells;
HT-29—Colon cancer cells.

As shown in Table 2, the compounds showed broad-spectrum anti-cancer activity. Interestingly, these complexes displayed enhanced anti-cancer activity towards cisplatin-resistant cancer cells (A2780Cis) and prostate cancer (PC-3) cells in comparison to compound 1 and cisplatin. In contrast, compound 1 showed the best activity towards cisplatin-sensitive (A2780) and colon (HT-29) cancer cells.

Compound 7 showed more than 92-fold and 2-fold better anti-cancer activity than cisplatin and auranofin, respectively, towards cisplatin-resistant ovarian cancer cells (A2780Cis).

Compound 1 exhibited approximately 13-fold higher activity than cisplatin against ovarian cancer cells (A2780).

Compound 8 displayed 45-fold and 3-fold better anti-cancer activity than cisplatin and auranofin, respectively, towards prostate cancer cells (PC3).

It is understood that the foregoing detailed description and accompanying examples are merely illustrative and are not to be taken as limitations upon the scope of the invention. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The claims defining the invention are as follows:

1. A compound according to Formula (I), or a pharmaceutically acceptable salt thereof:

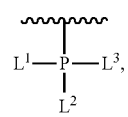

(I)

wherein:
R$^1$ and R$^2$ are each independently selected from optionally substituted C$_{1-6}$-alkyl and optionally substituted aryl;
R$^3$, R$^4$, R$^5$, and R$^6$ are each independently selected from the group consisting of H, halo, optionally substituted C$_{1-6}$-alkyl, and optionally substituted C$_{1-6}$ alkoxy; and
R$^7$ is a phosphorus containing moiety, wherein a phosphorus atom is bonded to Au.

2. The compound or pharmaceutically acceptable salt thereof according to claim 1, wherein R$^1$ and R$^2$ are optionally substituted aryl.

3. The compound or pharmaceutically acceptable salt thereof according to claim 1, wherein R$^3$ is selected from the group consisting of H, Br, Cl, F, methyl, ethyl, propyl and butyl and R4 is selected from the group consisting of H, Br, Cl, F, methyl, ethyl, propyl and butyl.

4. The compound or pharmaceutically acceptable salt thereof according to claim 1, wherein R$^5$ is H and R$^6$ is H.

5. The compound or pharmaceutically acceptable salt thereof according to claim 1, wherein R$^3$, R$^4$, R$^5$, and R$^6$ are H.

6. The compound or pharmaceutically acceptable salt thereof according to claim 1, wherein R$^7$ is:

$$L^1\text{—}P\text{—}L^3,$$
$$|$$
$$L^2$$

wherein L$^1$, L$^2$, and L$^3$ are each independently selected from optionally substituted aryl or optionally substituted heteroaryl; or two or more of L$^1$, L$^2$, or L$^3$, when taken together with the phosphorus atom to which they are attached, form an optionally substituted heterocyclic moiety.

7. The compound or pharmaceutically acceptable salt thereof according to claim 6, wherein L$^1$, L$^2$, and L$^3$ are each independently an optionally substituted aryl.

8. The compound or pharmaceutically acceptable salt thereof according to claim 7, wherein each aryl is phenyl.

9. The compound or pharmaceutically acceptable salt thereof according to claim 7, wherein the optionally substituted aryl is 3-phenylsulfonate.

10. The compound or pharmaceutically acceptable salt thereof according to claim 1, wherein R$^7$ is 1,3,5-triaza-7-phosphaadamantane (PTA).

11. The compound or pharmaceutically acceptable salt thereof according to claim 1, wherein the compound is selected from the group consisting of:

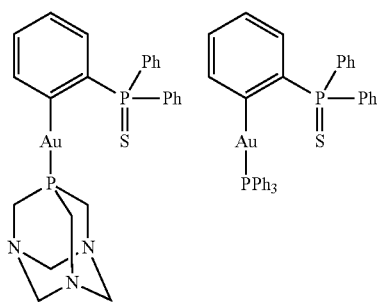
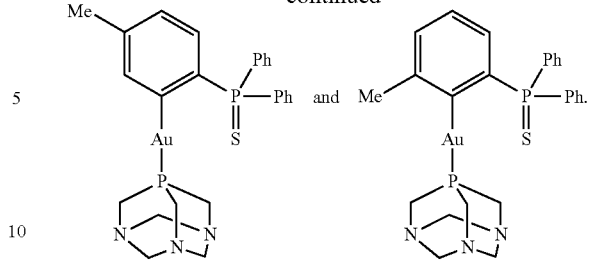
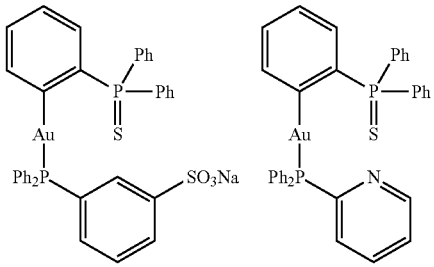
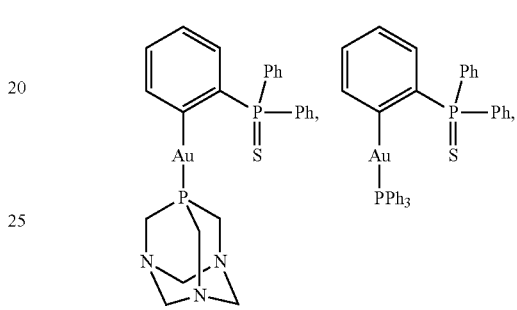
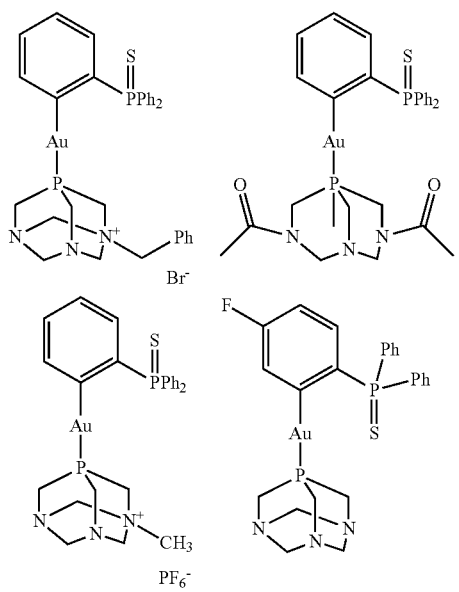
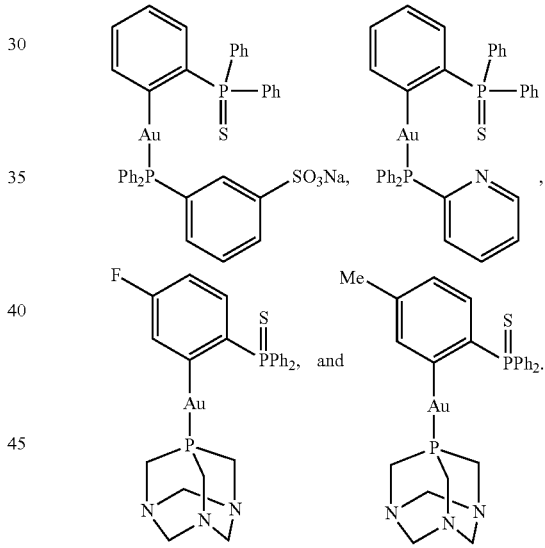
12. The compound or pharmaceutically acceptable salt thereof according to claim 1, wherein the compound is selected from the group consisting of:
13. A pharmaceutical composition comprising a compound according to claim 1 or a pharmaceutically acceptable salt thereof, and a pharmaceutically acceptable diluent, adjuvant, excipient, or carrier.
* * * * *